(12) United States Patent
Jimenez et al.

(10) Patent No.: US 11,452,699 B2
(45) Date of Patent: *Sep. 27, 2022

(54) METHOD OF TREATING OR PREVENTING TUMORS OF THE CENTRAL NERVOUS SYSTEM

(71) Applicant: Berg LLC, Framingham, MA (US)

(72) Inventors: Joaquin J. Jimenez, Miami, FL (US); Niven Rajin Narain, Cambridge, MA (US); Rangaprasad Sarangarajan, Boylston, MA (US); John Patrick McCook, Frisco, TX (US)

(73) Assignee: Berg LLC, Framingham, MA (US)

( * ) Notice: Subject to any disclaimer, the term of this patent is extended or adjusted under 35 U.S.C. 154(b) by 4 days.

This patent is subject to a terminal disclaimer.

(21) Appl. No.: 16/444,296

(22) Filed: Jun. 18, 2019

(65) Prior Publication Data

US 2020/0078320 A1     Mar. 12, 2020

Related U.S. Application Data

(63) Continuation of application No. 15/376,243, filed on Dec. 12, 2016, now Pat. No. 10,376,477, which is a continuation of application No. 13/439,615, filed on Apr. 4, 2012, now abandoned.

(60) Provisional application No. 61/471,659, filed on Apr. 4, 2011.

(51) Int. Cl.
*A61K 31/122* (2006.01)

(52) U.S. Cl.
CPC ................ *A61K 31/122* (2013.01)

(58) Field of Classification Search
CPC ... A61K 31/122; A61K 2300/00; A61P 27/16; A61P 35/04; A61P 27/10; A61P 25/18; A61P 25/00; A61P 21/00; A61P 35/00; A61P 1/08; A61P 25/06
See application file for complete search history.

(56) References Cited

U.S. PATENT DOCUMENTS

| 4,483,873 A | 11/1984 | Ohashi et al. |
| 4,515,736 A | 5/1985 | Deamer |
| 4,525,350 A | 6/1985 | Casey et al. |
| 4,636,381 A | 1/1987 | Takada et al. |
| 4,654,373 A | 3/1987 | Bertelli |

(Continued)

FOREIGN PATENT DOCUMENTS

| CA | 2553690 A1 | 8/2005 |
| CA | 2680825 A1 | 9/2008 |

(Continued)

OTHER PUBLICATIONS

Brain Tumors, Symptoms and Signs: https://www.cancer.net/cancer-types/brain-tumor/symptoms-and-signs, downloaded on Mar. 20, 2021. (Year: 2021).*

(Continued)

*Primary Examiner* — Melissa S Mercier
(74) *Attorney, Agent, or Firm* — McCarter & English, LLP; Jill Mello

(57) ABSTRACT

The invention provides methods and compositions for treatment of a subject with a central nervous system (CNS) tumor comprising administration of Coenzyme Q10 (CoQ10), particularly when the subject exhibits at least one CNS abnormality as a result of the tumor.

27 Claims, 4 Drawing Sheets

(56) References Cited

U.S. PATENT DOCUMENTS

| | | |
|---|---|---|
| 4,824,669 A | 4/1989 | Folkers et al. |
| 4,833,128 A | 5/1989 | Solomon et al. |
| 4,895,727 A | 1/1990 | Allen |
| 5,015,483 A | 5/1991 | Haynes et al. |
| 5,045,559 A | 9/1991 | Scott |
| 5,362,494 A | 11/1994 | Zysman et al. |
| 5,378,461 A | 1/1995 | Neigut |
| 5,527,789 A | 6/1996 | Nyce |
| 5,602,184 A | 2/1997 | Myers et al. |
| 5,603,958 A | 2/1997 | Morein et al. |
| 5,605,930 A | 2/1997 | Samid |
| 5,651,991 A | 7/1997 | Sugiyama et al. |
| 5,700,482 A | 12/1997 | Frederiksen et al. |
| 5,719,303 A | 2/1998 | Yoshida et al. |
| 5,770,222 A | 6/1998 | Unger et al. |
| 5,876,737 A | 3/1999 | Schonrock et al. |
| 5,889,062 A | 3/1999 | Hoppe et al. |
| 5,891,465 A | 4/1999 | Keller et al. |
| 5,912,272 A | 6/1999 | Hoppe et al. |
| 5,944,012 A | 8/1999 | Pera |
| 5,962,243 A | 10/1999 | Brown et al. |
| 6,005,086 A | 12/1999 | Evans et al. |
| 6,048,886 A | 4/2000 | Neigut |
| 6,063,820 A | 5/2000 | Cavazza |
| 6,071,495 A | 6/2000 | Unger et al. |
| 6,093,706 A | 7/2000 | Zeligs |
| 6,093,743 A | 7/2000 | Lai et al. |
| 6,184,353 B1 | 2/2001 | Evans et al. |
| 6,228,891 B1 | 5/2001 | Enzmann et al. |
| 6,261,575 B1 | 7/2001 | Hoppe et al. |
| 6,348,506 B2 | 2/2002 | Sneed |
| 6,372,234 B1 | 4/2002 | Deckers et al. |
| 6,403,116 B1 | 6/2002 | Anderson et al. |
| 6,416,957 B1 | 7/2002 | Evans et al. |
| 6,417,233 B1 | 7/2002 | Sears et al. |
| 6,441,050 B1 | 8/2002 | Chopra |
| 6,461,593 B1 | 10/2002 | Hanioka et al. |
| 6,465,517 B1 | 10/2002 | Van Der Zee |
| 6,468,552 B1 | 10/2002 | Stahl et al. |
| 6,469,061 B1 | 10/2002 | Flescher et al. |
| 6,482,943 B1 | 11/2002 | Blokhin et al. |
| 6,503,506 B1 | 1/2003 | Germano |
| 6,503,523 B2 | 1/2003 | Hoppe et al. |
| 6,506,915 B1 | 1/2003 | West |
| 6,511,800 B1 | 1/2003 | Singh |
| 6,531,117 B2 | 3/2003 | Heger et al. |
| 6,569,463 B2 | 5/2003 | Patel et al. |
| 6,573,284 B1 | 6/2003 | Riley et al. |
| 6,576,660 B1 | 6/2003 | Liao et al. |
| 6,576,678 B1 | 6/2003 | Bruening et al. |
| 6,582,710 B2 | 6/2003 | Deckers et al. |
| 6,582,723 B2 | 6/2003 | Gorsek |
| 6,596,287 B2 | 7/2003 | Deckers et al. |
| 6,599,513 B2 | 7/2003 | Deckers et al. |
| 6,623,746 B1 | 9/2003 | Wadle et al. |
| 6,630,160 B1 | 10/2003 | Evans et al. |
| 6,632,443 B2 | 10/2003 | Borowy-Borowski et al. |
| 6,652,891 B2 | 11/2003 | Selzer |
| 6,682,763 B2 | 1/2004 | Kuno et al. |
| 6,686,485 B2 | 2/2004 | West |
| 6,696,484 B2 | 2/2004 | Liao et al. |
| 6,726,924 B2 | 4/2004 | Keller |
| 6,727,234 B2 | 4/2004 | Wiemer et al. |
| 6,733,790 B1 | 5/2004 | Garces Garces |
| 6,753,325 B2 | 6/2004 | Rosenbloom |
| 6,803,193 B1 | 10/2004 | Hopper et al. |
| 6,806,069 B2 | 10/2004 | Chokshi |
| 6,809,176 B2 | 10/2004 | Blokhin et al. |
| 6,866,864 B2 | 3/2005 | Mousa |
| 6,867,024 B2 | 3/2005 | Chokshi |
| 6,906,106 B2 | 6/2005 | Chevalier |
| 6,923,988 B2 | 8/2005 | Patel et al. |
| 7,005,274 B1 | 2/2006 | Terkeltaub et al. |
| 7,060,733 B2 | 6/2006 | Pandol et al. |
| 7,083,572 B2 | 8/2006 | Unger et al. |
| 7,083,780 B2 | 8/2006 | Ansmann et al. |
| 7,091,241 B2 | 8/2006 | Gilloteaux et al. |
| 7,101,536 B2 | 9/2006 | Mongiat et al. |
| 7,132,268 B2 | 11/2006 | Miyake et al. |
| 7,147,841 B2 | 12/2006 | Herzog |
| 7,169,385 B2 | 1/2007 | Fantuzzi et al. |
| 7,169,590 B2 | 1/2007 | Ueda et al. |
| 7,176,171 B2 | 2/2007 | Nieendick et al. |
| 7,179,880 B2 | 2/2007 | Kawa et al. |
| 7,182,938 B2 | 2/2007 | Andre et al. |
| 7,182,950 B2 | 2/2007 | Garti et al. |
| 7,198,801 B2 | 4/2007 | Carrara et al. |
| 7,208,298 B2 | 4/2007 | Miyake et al. |
| 7,247,714 B2 | 7/2007 | Kunsch et al. |
| 7,250,174 B2 | 7/2007 | Lee et al. |
| 7,268,107 B2 | 9/2007 | Nieendick et al. |
| 7,273,606 B2 | 9/2007 | Fantuzzi et al. |
| 7,279,456 B2 | 10/2007 | Dufay et al. |
| 7,311,897 B2 | 12/2007 | Ehlis et al. |
| 7,318,929 B2 | 1/2008 | Schieferstein et al. |
| 7,357,918 B2 | 4/2008 | Comte et al. |
| 7,456,161 B2 | 11/2008 | Nyce |
| 7,635,722 B1 | 12/2009 | Bachynsky et al. |
| 7,776,894 B2 | 8/2010 | Ronai et al. |
| 7,824,673 B2 | 11/2010 | Wegman et al. |
| 7,858,659 B2 | 12/2010 | Hoffman et al. |
| 7,879,823 B2 | 2/2011 | Seiberg et al. |
| 7,906,140 B2 | 3/2011 | Bromley et al. |
| 8,147,825 B2 | 4/2012 | Hsia et al. |
| 8,293,227 B2 | 10/2012 | Hsia et al. |
| 8,562,976 B2 | 10/2013 | Hsia et al. |
| 8,586,030 B2 | 11/2013 | Hsia et al. |
| 8,746,515 B2 | 6/2014 | Fatherazi et al. |
| 8,771,680 B2 | 7/2014 | Hsia et al. |
| 9,205,064 B2 | 12/2015 | Narain et al. |
| 9,896,731 B2 | 2/2018 | Narain et al. |
| 9,901,542 B2 | 2/2018 | Narain et al. |
| 9,926,580 B2 | 3/2018 | Yajima et al. |
| 10,351,915 B2 | 7/2019 | Narain et al. |
| 10,376,477 B2 * | 8/2019 | Jimenez ............ A61P 27/16 |
| 10,519,504 B2 | 12/2019 | Narain et al. |
| 10,583,098 B2 | 3/2020 | Hsia et al. |
| 10,933,032 B2 | 3/2021 | Narain et al. |
| 11,028,446 B2 | 6/2021 | Narain et al. |
| 2001/0022965 A1 | 9/2001 | Heger et al. |
| 2001/0043909 A1 | 11/2001 | SaNogueira et al. |
| 2001/0053356 A1 | 12/2001 | Mousa |
| 2002/0039595 A1 | 4/2002 | Keller |
| 2002/0044913 A1 | 4/2002 | Hamilton |
| 2002/0045230 A1 | 4/2002 | Rosen et al. |
| 2002/0048559 A1 | 4/2002 | Shinoda et al. |
| 2002/0048798 A1 | 4/2002 | Avery et al. |
| 2002/0049176 A1 | 4/2002 | Anderson et al. |
| 2002/0049253 A1 | 4/2002 | Kaddurah-Daouk |
| 2002/0049422 A1 | 4/2002 | Brewitt |
| 2002/0058712 A1 | 5/2002 | Sneed |
| 2002/0071852 A1 | 6/2002 | Deckers et al. |
| 2002/0091288 A1 | 7/2002 | Wilbur et al. |
| 2002/0098169 A1 | 7/2002 | Smith |
| 2002/0106337 A1 | 8/2002 | Deckers et al. |
| 2002/0114820 A1 | 8/2002 | Deckers et al. |
| 2002/0127252 A1 | 9/2002 | Kramer et al. |
| 2002/0136711 A1 | 9/2002 | Cochran |
| 2002/0146463 A1 | 10/2002 | Clayton |
| 2002/0155151 A1 | 10/2002 | Enzmann et al. |
| 2002/0156302 A1 | 10/2002 | West |
| 2002/0164317 A1 | 11/2002 | Gorsek |
| 2002/0182199 A1 | 12/2002 | Hoppe et al. |
| 2002/0198177 A1 | 12/2002 | Horrobin |
| 2003/0012762 A1 | 1/2003 | Zulli et al. |
| 2003/0012779 A1 | 1/2003 | Grieb et al. |
| 2003/0012825 A1 | 1/2003 | Kapper |
| 2003/0031688 A1 | 2/2003 | Ghosh et al. |
| 2003/0044441 A1 | 3/2003 | Schmid et al. |
| 2003/0077297 A1 | 4/2003 | Chen et al. |
| 2003/0077335 A1 | 4/2003 | Richardson et al. |
| 2003/0087331 A1 | 5/2003 | Pettit et al. |
| 2003/0091518 A1 | 5/2003 | Pauly et al. |
| 2003/0103954 A1 | 6/2003 | Rosenbloom |

(56) References Cited

U.S. PATENT DOCUMENTS

| | | |
|---|---|---|
| 2003/0104048 A1 | 6/2003 | Patel et al. |
| 2003/0104080 A1 | 6/2003 | Singh et al. |
| 2003/0105027 A1 | 6/2003 | Rosenbloom |
| 2003/0105030 A1 | 6/2003 | Liao et al. |
| 2003/0105031 A1 | 6/2003 | Rosenbloom |
| 2003/0108493 A1 | 6/2003 | Henry et al. |
| 2003/0113354 A1 | 6/2003 | Schmid et al. |
| 2003/0118525 A1 | 6/2003 | Grigg |
| 2003/0118536 A1 | 6/2003 | Rosenbloom |
| 2003/0118576 A1 | 6/2003 | Brancato et al. |
| 2003/0124158 A1 | 7/2003 | Heidenfelder et al. |
| 2003/0129150 A1 | 7/2003 | Pauly et al. |
| 2003/0138792 A1 | 7/2003 | Schlegel et al. |
| 2003/0143166 A1 | 7/2003 | Heger et al. |
| 2003/0144346 A1 | 7/2003 | Liao et al. |
| 2003/0152598 A1 | 8/2003 | Heidenfelder et al. |
| 2003/0161849 A1 | 8/2003 | Heidenfelder et al. |
| 2003/0167556 A1 | 9/2003 | Kelley |
| 2003/0170265 A1 | 9/2003 | Henry et al. |
| 2003/0180231 A1 | 9/2003 | Danoux et al. |
| 2003/0180278 A1 | 9/2003 | Hoppe et al. |
| 2003/0180352 A1 | 9/2003 | Patel et al. |
| 2003/0185865 A1 | 10/2003 | Jentzsch et al. |
| 2003/0207834 A1 | 11/2003 | Dale et al. |
| 2003/0212114 A1 | 11/2003 | Sato |
| 2003/0215406 A1 | 11/2003 | Schreiner et al. |
| 2003/0219472 A1 | 11/2003 | Pauletti et al. |
| 2003/0235812 A1 | 12/2003 | Anderson et al. |
| 2004/0028614 A1 | 2/2004 | Corbella et al. |
| 2004/0028668 A1 | 2/2004 | Gaetani |
| 2004/0034107 A1 | 2/2004 | Enzmann |
| 2004/0043045 A1 | 3/2004 | Seipel et al. |
| 2004/0047896 A1 | 3/2004 | Malnoe et al. |
| 2004/0049022 A1 | 3/2004 | Nyce et al. |
| 2004/0063648 A1 | 4/2004 | Pandol et al. |
| 2004/0063661 A1 | 4/2004 | Linnane |
| 2004/0067260 A1 | 4/2004 | Milley et al. |
| 2004/0082522 A1 | 4/2004 | Nyce |
| 2004/0086538 A1 | 5/2004 | Sauermann et al. |
| 2004/0101874 A1 | 5/2004 | Ghosh et al. |
| 2004/0109880 A1 | 6/2004 | Pauly et al. |
| 2004/0110848 A1 | 6/2004 | Peffley et al. |
| 2004/0115181 A1 | 6/2004 | Fujii et al. |
| 2004/0122109 A1 | 6/2004 | Fujii et al. |
| 2004/0126367 A1 | 7/2004 | Fujii et al. |
| 2004/0133352 A1 | 7/2004 | Bevilacqua et al. |
| 2004/0142006 A1 | 7/2004 | Bleckmann et al. |
| 2004/0142007 A1 | 7/2004 | Moussou et al. |
| 2004/0142009 A1 | 7/2004 | Ansmann et al. |
| 2004/0151710 A1 | 8/2004 | Bozzacco |
| 2004/0151711 A1 | 8/2004 | West |
| 2004/0170560 A1 | 9/2004 | Fossheim et al. |
| 2004/0170581 A1 | 9/2004 | Henry et al. |
| 2004/0185071 A1 | 9/2004 | Hatazaki |
| 2004/0191190 A1 | 9/2004 | Pauly et al. |
| 2004/0191263 A1 | 9/2004 | Hageman et al. |
| 2004/0197279 A1 | 10/2004 | Bleckmann et al. |
| 2004/0197354 A1 | 10/2004 | Doring et al. |
| 2004/0202740 A1 | 10/2004 | Tan |
| 2004/0219114 A1 | 11/2004 | Andersson et al. |
| 2004/0228910 A1 | 11/2004 | Enzmann et al. |
| 2004/0234559 A1 | 11/2004 | Bleckmann et al. |
| 2004/0253323 A1 | 12/2004 | Giles |
| 2004/0258717 A1 | 12/2004 | Sauermann et al. |
| 2005/0000390 A1 | 1/2005 | Nieendick et al. |
| 2005/0008581 A1 | 1/2005 | Parkhideh |
| 2005/0019268 A1 | 1/2005 | Enzmann |
| 2005/0019278 A1 | 1/2005 | Berg-Schultz |
| 2005/0019353 A1 | 1/2005 | Prinz et al. |
| 2005/0025756 A1 | 2/2005 | Erwin |
| 2005/0026848 A1 | 2/2005 | Robinson et al. |
| 2005/0026850 A1 | 2/2005 | Robinson et al. |
| 2005/0036976 A1 | 2/2005 | Rubin et al. |
| 2005/0037036 A1 | 2/2005 | Nielsen et al. |
| 2005/0037102 A1 | 2/2005 | Tan et al. |
| 2005/0042678 A1 | 2/2005 | Epstein et al. |
| 2005/0043336 A1 | 2/2005 | Hennequin et al. |
| 2005/0058610 A1 | 3/2005 | Baschong et al. |
| 2005/0069582 A1 | 3/2005 | Fantuzzi |
| 2005/0070610 A1 | 3/2005 | Fujii et al. |
| 2005/0070611 A1 | 3/2005 | Fantuzzi |
| 2005/0079164 A1 | 4/2005 | Fantuzzi et al. |
| 2005/0100537 A1 | 5/2005 | Evans et al. |
| 2005/0106190 A1 | 5/2005 | Kawa et al. |
| 2005/0106199 A1 | 5/2005 | Schreiber et al. |
| 2005/0112156 A1 | 5/2005 | Busch et al. |
| 2005/0118151 A1 | 6/2005 | Larsen et al. |
| 2005/0118209 A1 | 6/2005 | Jentszch et al. |
| 2005/0136081 A1 | 6/2005 | Kawa et al. |
| 2005/0142123 A1 | 6/2005 | Chen et al. |
| 2005/0142153 A1 | 6/2005 | Schreiber et al. |
| 2005/0147598 A1 | 7/2005 | Ueda et al. |
| 2005/0148603 A1 | 7/2005 | Jimenez et al. |
| 2005/0152856 A2 | 7/2005 | Andersson et al. |
| 2005/0184275 A1 | 8/2005 | Mora-Gutierrez et al. |
| 2005/0202521 A1 | 9/2005 | Crum |
| 2005/0214333 A1 | 9/2005 | Lanzendoerfer et al. |
| 2005/0220726 A1 | 10/2005 | Pauly et al. |
| 2005/0220826 A1 | 10/2005 | Kawa et al. |
| 2005/0226824 A1 | 10/2005 | Kawa et al. |
| 2005/0226858 A1 | 10/2005 | Kitamura et al. |
| 2005/0226947 A1 | 10/2005 | Kern |
| 2005/0238679 A1 | 10/2005 | Biergiesser et al. |
| 2005/0239721 A1 | 10/2005 | Rosenbloom |
| 2005/0255057 A1 | 11/2005 | Andre et al. |
| 2005/0276764 A1 | 12/2005 | Kolbe et al. |
| 2005/0281772 A1 | 12/2005 | Bromley et al. |
| 2005/0287206 A1 | 12/2005 | Fantuzzi et al. |
| 2005/0288333 A1 | 12/2005 | Kem |
| 2005/0288378 A1 | 12/2005 | Yan et al. |
| 2006/0002911 A1 | 1/2006 | Casteilla et al. |
| 2006/0002964 A9 | 1/2006 | Schreiber et al. |
| 2006/0008482 A1 | 1/2006 | Prinz et al. |
| 2006/0010519 A1 | 1/2006 | Kadowaki et al. |
| 2006/0013888 A1 | 1/2006 | Fantuzzi |
| 2006/0035981 A1 | 2/2006 | Mazzio et al. |
| 2006/0039956 A1 | 2/2006 | Hensen et al. |
| 2006/0041017 A1 | 2/2006 | Chopra |
| 2006/0051462 A1 | 3/2006 | Wang |
| 2006/0052438 A1 | 3/2006 | Ho et al. |
| 2006/0057081 A1 | 3/2006 | Boxrud |
| 2006/0062755 A1 | 3/2006 | Woodward |
| 2006/0069068 A1 | 3/2006 | Kajander et al. |
| 2006/0073106 A1 | 4/2006 | Berg-Schultz et al. |
| 2006/0093633 A1 | 5/2006 | Stab et al. |
| 2006/0099158 A1 | 5/2006 | Zander et al. |
| 2006/0099244 A1 | 5/2006 | Guilford |
| 2006/0110415 A1 | 5/2006 | Gupta |
| 2006/0120997 A1 | 6/2006 | Lipton |
| 2006/0121016 A1 | 6/2006 | Lee |
| 2006/0127384 A1 | 6/2006 | Capaccioli et al. |
| 2006/0127928 A1 | 6/2006 | Bacus et al. |
| 2006/0128643 A1 | 6/2006 | Kaddurah-Daouk et al. |
| 2006/0153783 A1 | 7/2006 | Ehlis et al. |
| 2006/0188459 A1 | 8/2006 | Heinrichs et al. |
| 2006/0188492 A1 | 8/2006 | Richardson et al. |
| 2006/0193905 A1 | 8/2006 | Ehringer et al. |
| 2006/0205771 A1 | 9/2006 | Noble et al. |
| 2006/0251690 A1 | 11/2006 | Lipshutz et al. |
| 2006/0251708 A1 | 11/2006 | Chen et al. |
| 2006/0252042 A1 | 11/2006 | Molero |
| 2006/0286046 A1 | 12/2006 | Haber |
| 2006/0292220 A1 | 12/2006 | Giordano et al. |
| 2007/0021360 A1 | 1/2007 | Nyce et al. |
| 2007/0026072 A1 | 2/2007 | Olsen et al. |
| 2007/0053985 A1 | 3/2007 | Ueda et al. |
| 2007/0054282 A1 | 3/2007 | Liew |
| 2007/0071779 A1 | 3/2007 | McKie |
| 2007/0085059 A1 | 4/2007 | Mora-Gutierrez et al. |
| 2007/0092469 A1 | 4/2007 | Jacobs |
| 2007/0104701 A1 | 5/2007 | Ueda et al. |
| 2007/0104810 A1 | 5/2007 | Kern |
| 2007/0110731 A1 | 5/2007 | Riley |
| 2007/0129428 A1 | 6/2007 | Richelle et al. |

(56) References Cited

U.S. PATENT DOCUMENTS

| | | |
|---|---|---|
| 2007/0149618 A1 | 6/2007 | Cuevas Sanchez et al. |
| 2007/0172436 A1 | 7/2007 | Zhang |
| 2007/0184041 A1 | 8/2007 | Burja |
| 2007/0184076 A1 | 8/2007 | Unger et al. |
| 2007/0189994 A1 | 8/2007 | Berg et al. |
| 2007/0196349 A1 | 8/2007 | Kitamura et al. |
| 2007/0196914 A1 | 8/2007 | Murray et al. |
| 2007/0202090 A1 | 8/2007 | Prosek et al. |
| 2007/0202496 A1 | 8/2007 | Beretta |
| 2007/0203091 A1 | 8/2007 | Rapaport |
| 2007/0218042 A1 | 9/2007 | Khaled |
| 2007/0225255 A1 | 9/2007 | Frohlich et al. |
| 2007/0243180 A1 | 10/2007 | Tanaka et al. |
| 2007/0248590 A1 | 10/2007 | Milne et al. |
| 2007/0248693 A1 | 10/2007 | Mazzio et al. |
| 2007/0253941 A1 | 11/2007 | Naidu et al. |
| 2007/0258966 A1 | 11/2007 | Ueda et al. |
| 2007/0258967 A1 | 11/2007 | Ueda et al. |
| 2007/0259009 A1 | 11/2007 | Linder |
| 2007/0275021 A1 | 11/2007 | Lee et al. |
| 2008/0014187 A1 | 1/2008 | Villeponteau |
| 2008/0020018 A1 | 1/2008 | Moodley et al. |
| 2008/0020022 A1 | 1/2008 | Udell |
| 2008/0025929 A1 | 1/2008 | Burton et al. |
| 2008/0031862 A1 | 2/2008 | Ghosal |
| 2008/0038736 A1 | 2/2008 | Llovet et al. |
| 2008/0057116 A1 | 3/2008 | Pleva |
| 2008/0063674 A1 | 3/2008 | Vollhardt et al. |
| 2008/0069779 A1 | 3/2008 | Tamarkin et al. |
| 2008/0069898 A1 | 3/2008 | Smith et al. |
| 2008/0075684 A1 | 3/2008 | Barg et al. |
| 2008/0081034 A1 | 4/2008 | Zimmerman et al. |
| 2008/0081082 A1 | 4/2008 | Zimmerman et al. |
| 2008/0089852 A1 | 4/2008 | Hotz et al. |
| 2008/0089913 A1 | 4/2008 | Kallmayer et al. |
| 2008/0095719 A1 | 4/2008 | Herrmann et al. |
| 2008/0102313 A1 | 5/2008 | Nilsen et al. |
| 2008/0138326 A1 | 6/2008 | Fujii et al. |
| 2008/0233183 A1 | 9/2008 | McCook et al. |
| 2008/0260878 A1 | 10/2008 | Harano et al. |
| 2008/0287541 A1* | 11/2008 | Hoffman ............... A61K 45/06 514/562 |
| 2008/0299100 A1 | 12/2008 | Hsia et al. |
| 2009/0005398 A1 | 1/2009 | Dar |
| 2009/0010917 A1 | 1/2009 | Rosenblum et al. |
| 2009/0036516 A1 | 2/2009 | Scherrer et al. |
| 2009/0060891 A1 | 3/2009 | Harris et al. |
| 2009/0068281 A1 | 3/2009 | Toyomura et al. |
| 2009/0137556 A1 | 5/2009 | Bonnichsen |
| 2009/0280987 A1 | 11/2009 | Strobel |
| 2010/0062048 A1 | 3/2010 | Hsia et al. |
| 2010/0150894 A1 | 6/2010 | Wakabayashi et al. |
| 2010/0209388 A1* | 8/2010 | Mazzio ............... A61K 36/54 424/85.4 |
| 2010/0239652 A1 | 9/2010 | Rochlitz et al. |
| 2011/0020312 A1 | 1/2011 | Narain et al. |
| 2011/0064747 A1 | 3/2011 | Sarangarajan et al. |
| 2011/0123550 A1 | 5/2011 | Shibayama et al. |
| 2011/0123986 A1 | 5/2011 | Narain et al. |
| 2011/0129503 A1 | 6/2011 | Strober et al. |
| 2011/0136231 A1 | 6/2011 | Narain et al. |
| 2011/0142914 A1 | 6/2011 | Persaud et al. |
| 2011/0229554 A1 | 9/2011 | Narain et al. |
| 2012/0164215 A1 | 6/2012 | Hsia et al. |
| 2012/0183621 A1 | 7/2012 | Sinko et al. |
| 2012/0201801 A1 | 8/2012 | Hsia et al. |
| 2012/0269867 A1 | 10/2012 | Jimenez et al. |
| 2012/0309086 A1 | 12/2012 | Narain et al. |
| 2013/0203853 A1 | 8/2013 | Jacobson |
| 2014/0017317 A1 | 1/2014 | Narain et al. |
| 2014/0255372 A1 | 9/2014 | Hsia et al. |
| 2015/0023940 A1 | 1/2015 | Narain et al. |
| 2015/0157559 A1 | 6/2015 | Narain et al. |
| 2016/0145693 A1 | 5/2016 | Narain et al. |
| 2017/0137879 A1 | 5/2017 | Narain et al. |
| 2017/0189350 A1 | 7/2017 | Narain et al. |
| 2017/0216223 A1 | 8/2017 | Narain et al. |
| 2018/0021270 A1 | 1/2018 | Nastke et al. |
| 2018/0334721 A1 | 11/2018 | Narain et al. |
| 2018/0353425 A1 | 12/2018 | Narain et al. |
| 2019/0010554 A1 | 1/2019 | Narain et al. |
| 2020/0138744 A1 | 5/2020 | Sarangarajan et al. |
| 2021/0002725 A1 | 1/2021 | Narain et al. |
| 2021/0128453 A1 | 5/2021 | Hsia et al. |

FOREIGN PATENT DOCUMENTS

| | | | |
|---|---|---|---|
| CA | 2791693 | A1 | 9/2011 |
| CN | 1535605 | A | 10/2004 |
| CN | 1853507 | A | 11/2006 |
| CN | 1928556 | A | 3/2007 |
| CN | 1953743 | A | 4/2007 |
| CN | 101099084 | A | 1/2008 |
| CN | 101102768 | A | 1/2008 |
| CN | 101365806 | A | 2/2009 |
| EA | 201001624 | A1 | 6/2011 |
| EP | 1473043 | A1 | 11/2004 |
| EP | 1493437 | A1 | 1/2005 |
| EP | 1908459 | A1 | 4/2008 |
| EP | 2028492 | A1 | 2/2009 |
| EP | 2371362 | A1 | 10/2011 |
| EP | 2371363 | A1 | 10/2011 |
| EP | 2429512 | A2 | 3/2012 |
| EP | 2854528 | A1 | 4/2015 |
| JP | S57-075916 | A | 5/1982 |
| JP | S62-123113 | A | 6/1987 |
| JP | H01-143826 | A | 6/1989 |
| JP | H02-273619 | A | 11/1990 |
| JP | 2001-514209 | A | 9/2001 |
| JP | 2004-345988 | A | 12/2004 |
| JP | 2005-323573 | A | 11/2005 |
| JP | 2007-001922 | A | 1/2007 |
| JP | 2007-176804 | A | 7/2007 |
| JP | 2007-518805 | A | 7/2007 |
| JP | 2009-050168 | A | 3/2009 |
| JP | 2009-096757 | A | 5/2009 |
| JP | 2012-510932 | A | 5/2012 |
| JP | 2015-151900 | A | 8/2015 |
| JP | 2018-109093 | A | 7/2018 |
| JP | 2018-168164 | A | 11/2018 |
| KR | 10-2005-0112942 | A | 12/2005 |
| RU | 2307666 | C2 | 10/2007 |
| RU | 2345367 | | 1/2009 |
| WO | WO-1988/04173 | A1 | 6/1988 |
| WO | WO-1993/016704 | A1 | 9/1993 |
| WO | WO-1994/11547 | A1 | 5/1994 |
| WO | WO-1995/05164 | A1 | 2/1995 |
| WO | WO-1995/10271 | A2 | 4/1995 |
| WO | WO-1996/017626 | A2 | 6/1996 |
| WO | WO-1998/35660 | A1 | 8/1998 |
| WO | WO-1999/11242 | A1 | 3/1999 |
| WO | WO-1999/65469 | A2 | 12/1999 |
| WO | WO-2000/007607 | A1 | 2/2000 |
| WO | WO-2002/40012 | A1 | 5/2002 |
| WO | WO-2002/060484 | A1 | 8/2002 |
| WO | WO-2002/062329 | A1 | 8/2002 |
| WO | WO-2002/062338 | A1 | 8/2002 |
| WO | WO-2002/078727 | A1 | 10/2002 |
| WO | WO-2002/085297 | A2 | 10/2002 |
| WO | WO-2003/008405 | A1 | 1/2003 |
| WO | WO-2003/077895 | A1 | 9/2003 |
| WO | WO-2003/078456 | A2 | 9/2003 |
| WO | WO-2004/003564 | A2 | 1/2004 |
| WO | WO-2004/059293 | A2 | 7/2004 |
| WO | WO-2004/060316 | A2 | 7/2004 |
| WO | WO-2005/055738 | A1 | 6/2005 |
| WO | WO-2005/069916 | A2 | 8/2005 |
| WO | WO-2006/017494 | A2 | 2/2006 |
| WO | WO-2006/063402 | A1 | 6/2006 |
| WO | WO-2007/039184 | A2 | 4/2007 |
| WO | WO-2007/095186 | A2 | 8/2007 |
| WO | WO-2007/131047 | A2 | 11/2007 |
| WO | WO-2008/049330 | A1 | 5/2008 |
| WO | WO-2008/116135 | A2 | 9/2008 |

(56) References Cited

FOREIGN PATENT DOCUMENTS

| | | |
|---|---|---|
| WO | WO-2008/156654 A2 | 12/2008 |
| WO | WO-2009/005215 A1 | 1/2009 |
| WO | WO-2009/006366 A2 | 1/2009 |
| WO | WO-2009/012718 A1 | 1/2009 |
| WO | WO-2009/014639 A2 | 1/2009 |
| WO | WO-2009/073843 A1 | 6/2009 |
| WO | WO-2009/126764 A1 | 10/2009 |
| WO | WO-2010/065601 A1 | 6/2010 |
| WO | WO-2010/132440 A2 | 11/2010 |
| WO | WO-2010/132507 A2 | 11/2010 |
| WO | WO-2011/031503 A2 | 3/2011 |
| WO | WO-2011/112900 A2 | 9/2011 |
| WO | WO-2012/012347 A2 | 1/2012 |
| WO | WO-2012/138765 A1 | 10/2012 |
| WO | WO-2013/181639 A1 | 12/2013 |
| WO | WO-2014/168993 A1 | 10/2014 |
| WO | WO-2015/035094 A1 | 3/2015 |
| WO | WO-2016/054574 A1 | 4/2016 |
| WO | WO-2016/062722 A1 | 4/2016 |
| WO | WO-2016/094639 A1 | 6/2016 |

OTHER PUBLICATIONS

Pediatric Leukemia, Children's Hospital of Philadelphia:: https://www.chop.edu/conditions-diseases/pediatric-leukemias, downloaded on Mar. 19, 2021. (Year: 2021).*
Stafford et al., Meningioma Radiosurgery: Tumor Control, Outcomes, and Complications among 190 Consecutive Patients, Neurosurgery 49:1029-1038, 2001. (Year: 2001).*
Ohanian et al., Is acute myeloid leukemia a liquid tumor? Int J Cancer. Aug. 1, 2013;133(3):534-43.
Abe et al., Effect of coenzyme Q10 in patients with mitochondrial myopathy, encephalopathy, lactic acidosis, and stroke-like episodes (MELAS): evaluation by noninvasive tissue oximetry. J Neurol Sci. Jan. 1, 1999;162(1):65-8.
Abe et al., Marked reduction in CSF lactate and pyruvate levels after CoQ therapy in a patient with mitochondrial myopathy, encephalopathy, lactic acidosis and stroke-like episodes (MELAS). Acta Neurol Scand. Jun. 1991;83(6):356-9.
Aizawa, Morphology of polysorbate 80 (Tween 80) micelles in aqueous dimethyl sulfoxide solutions. J Appl Crystallogr. Jun. 1, 2010;43(Pt 3):630-631.
American Cancer Society, Brain and Spinal Cord Tumors in Adults. Retrieved online at: http://www.cancer.org/cancer/braincnstumorsinadults/detailedguide/brain-and-spinal-cord-tumors-in-adults-what-are-brain-spinal-tumors. Nov. 12, 2009. 4 pages.
American Cancer Society, Colorectal Cancer. Retrieved online at: http:www.cancer.org/acs/groups/cid/documents/webcontent/003096-pdf.pdf. 122 pages, (2016).
Anderson et al., The transcriptional response to a peroxisome proliferator-activated receptor alpha agonist includes increased expression of proteome maintenance genes. J Biol Chem. Dec. 10, 2004;279(50):52390-8.
Ansell et al., Brain tumor signs and symptoms: analysis of primary health care records from the UKCCS. Pediatrics. Jan. 2010;125(1):112-9.
Antoneeva et al., Markers of Apoptosis and Proliferation of Tumor Cells in the Dynamic of Ovarian Cancer Progression. Oncologiya. 2008;10(2):234-237.
Aris et al., Noise filtering and nonparametric analysis of microarray data underscores discriminating markers of oral, prostate, lung, ovarian and breast cancer. BMC Bioinformatics. Nov. 29, 2004;5(185):1-9.
Barbiroli et al., Coenzyme Q10 improves mitochondrial respiration in patients with mitochondrial cytopathies. An in vivo study on brain and skeletal muscle by phosphorous magnetic resonance spectroscopy. Cell Mol Biol (Noisy-le-grand). Jul. 1997;43(5):741-9.
Bjarnason, Chronobiology. Implications for cancer chemotherapy. Acta Oncol. 1995;34(5):615-24.

Bliznakov et al., Coenzymes Q: stimulants of the phagocytic activity in rats and immune response in mice. Experientia. Sep. 26, 1970;26(9):953-4.
Bliznakov, Effect of stimulation of the host defense system by coenzyme Q 0 on dibenzpyrene-induced tumors and infection with Friend leukemia virus in mice. Proc Natl Acad Sci U S A. Feb. 1973;70(2):390-4.
Blom et al., The risk of a venous thrombotic event in lung cancer patients: higher risk for adenocarcinoma than squamous cell carcinoma. J Thromb Haemost. Oct. 2004;2(10):1760-5.
Bresolin et al., Clinical and biochemical correlations in mitochondrial myopathies treated with coenzyme Q10. Neurology. Jun. 1988;38(6):892-9.
Carmona et al., Coadministration of coenzyme Q prevents rosiglitazone-induced adipogenesis in ob/ob mice. Int J Obes (Lond). Feb. 2009;33(2):204-11.
Chan et al., Metabolic changes in patients with mitochondrial myopathies and effects of coenzyme Q10 therapy. J Neurol. Oct. 1998;245(10):681-5.
Chang et al., Patterns of resistance and incomplete response to docetaxel by gene expression profiling in breast cancer patients. J Clin Oncol. Feb. 20, 2005;23(6):1169-77.
Chen et al., Coenzyme Q10 treatment in mitochondrial encephalomyopathies. Short-term double-blind, crossover study. Eur Neurol. 1997;37(4):212-8.
Cheung et al., Novel markers of subclinical disease for Ewing family tumors from gene expression profiling. Clin Cancer Res. Dec. 1, 2007;13(23):6978-83.
Chew et al., Coenzyme Q10 and diabetic endotheliopathy: oxidative stress and the 'recoupling hypothesis'. QJM. Aug. 2004;97(8):537-48.
ClinicalTrials.gov, NCT01928394, A Study of Nivolumab by Itself or Nivolumab Combined With Ipilimumab in Patients With Advanced or Metastatic Solid Tumors. 9 pages, Oct. 4, 2019.
Colman et al., Hemostasis and Thrombosis. Basic Principles and Clinical Practice, 5th Edition, Lippincott Williams & Wilkins, p. 1161 (2006).
Colon cancer: Tests and diagnosis—MayoClinic.com. Retrieved online at: http://www.mayoclinic.com/health/colon-cancer/ds00035/dsection=tests-and-diagnosis. 3 pages, Aug. 13, 2011.
Conklin, Cancer chemotherapy and antioxidants. J Nutr. Nov. 2004;134(11):3201S-3204S.
Conklin, Coenzyme q10 for prevention of anthracycline-induced cardiotoxicity. Integr Cancer Ther. Jun. 2005;4(2):110-30.
Crane, New Functions for Coenzyme Q. Protoplasma. 2000;213:127-133.
Crawford et al., Multiplex standardized RT-PCR for expression analysis of many genes in small samples. Biochem Biophys Res Commun. Apr. 26, 2002;293(1):509-16.
De Oliveria, A Nutritious Cocktail for the Treatment of Melanoma: A Case Report. The Journal of Orthomolecular Medicine. 1998;13(3)13, 2 pages.
Deeb et al., Vitamin D signalling pathways in cancer: potential for anticancer therapeutics. Nat Rev Cancer. Sep. 2007;7(9):684-700.
Doi et al., The JAK/STAT pathway is involved in the upregulation of PD-L1 expression in pancreatic cancer cell lines. Oncol Rep. 2017;37(3):1545-1554.
Domae et al., Cardiomyopathy and other chronic toxic effects induced in rabbits by doxorubicin and possible prevention by coenzyme Q10. Cancer Treat Rep. Jan.-Feb. 1981;65(1-2):79-91.
Eisenhauer et al., New response evaluation criteria in solid tumours: Revised RECIST guideline (version 1.1). European Journal of Cancer. 2009;45:228-247.
Family Caregiver Alliance, Fact Sheet: Brain Tumor. Los Angeles Caregiver Resource Center. Retrieved online at: http://lacrc.usc.edu/forms/brain tumor.pdf. 12 pages (2004).
Fang et al., Expression of ectonucleotide pyrophosphatase/phosphodiesterase 1 in human ovary and its relationship with polycystic ovary syndrome. ACTA Anatomica Sinica. 2008;39(4):552-556.

(56) References Cited

OTHER PUBLICATIONS

Fernández-Ayala et al., Coenzyme Q protects cells against serum withdrawal-induced apoptosis by inhibition of ceramide release and caspase-3 activation. Antioxid Redox Signal. 2000 Summer;2(2):263-75.

Ferrara et al., Protective role of chronic ubiquinone administration on acute cardiac oxidative stress. J Pharmacol Exp Ther. Aug. 1995;274(2):858-65.

Folkers, Relevance of the biosynthesis of coenzyme Q10 and of the four bases of DNA as a rationale for the molecular causes of cancer and a therapy. Biochem Biophys Res Commun. Jul. 16, 1996;224(2):358-61.

Foulkes et al., Triple-negative breast cancer. N Engl J Med. Nov. 11, 2010;363(20):1938-48.

Friedman et al., Temozolomide and Treatment of Malignant Glioma. Clinical Cancer Research. Jul. 2000;6:2585-2597, plus supplemental material.

Gaby, The Role of Coenzyme Q10 in Clinical Medicine: Part I. Alt Med Rev. 1996;1:11-17.

Galili et al., Clinical response of myelodysplastic syndromes patients to treatment with coenzyme Q10. Leuk Res. Jan. 2007;31(1):19-26.

Gao et al., Effects of coenzyme Q10 on vascular endothelial function in humans: a meta-analysis of randomized controlled trials. Atherosclerosis. Apr. 2012;221(2):311-6.

Garrel et al., The diagnostic accuracy of reverse transcription-PCR quantification of cytokeratin mRNA in the detection of sentinel lymph node invasion in oral and oropharyngeal squamous cell carcinoma: a comparison with immunohistochemistry. Clin Cancer Res. Apr. 15, 2006;12(8):2498-505.

Gersten, Brain Cancer Overview. The New York Times. Retrieved online at: http://health.nytimes.com/health/guides/disease/brain-tumor-adults. 3 pages.

Gogvadze et al., Mitochondria as targets for chemotherapy. Apoptosis. Apr. 2009;14(4):624-40.

Golay et al., Link between obesity and type 2 diabetes. Best Pract Res Clin Endocrinol Metab. Dec. 2005;19(4):649-63.

Gorelick et al., Coenzyme Q10 and lipid-related gene induction in HeLa cells. Am J Obstet Gynecol. May 2004;190(5):1432-4.

Groneberg et al., Coenzyme Q10 affects expression of genes involved in cell signaling, metabolism and transport in human CaCo-2 cells. The International Journal of Biochemistry and Cell Biology. 2005;37:1208-1218.

Haider et al., Effects of etanercept are distinct from infliximab in modulating proinflammatory genes in activated human leukocytes. J Investig Dermatol Symp Proc. May 2007;12(1):9-15.

Happold et al., Distinct molecular mechanisms of acquired resistance to temozolomide in glioblastoma cells. J Neurochem. Jul. 2012;122(2):444-55.

Higdon et al., Obesity and oxidative stress: a direct link to CVD? Arterioscler Thromb Vase Biol. Mar. 1, 2003;23(3):365-7.

Hill et al., Pharmacokinetics of drug infusions. Continuing Education in Anaesthesia. 2004. 4(3):76-80.

Hodges et al., CoQ10: could it have a role in cancer management? Biofactors. 1999;9(2-4):365-70.

Hodgson et al., Coenzyme Q10 improves blood pressure and glycaemic control: a controlled trial in subjects with type 2 diabetes. Eur J Clin Nutr. Nov. 2002;56(11):1137-42.

Huang et al., Treatment of refractory recurrent malignant glioma with adoptive cellular immunotherapy: a case report. Critical Reviews in Oncology/Hematology. 2001;57:17-23.

Hudson et al., Characterization of potentially chemopreventive phenols in extracts of brown rice that inhibit the growth of human breast and colon cancer cells. Cancer Epidemiol Biomarkers Prev. Nov. 2000;9(11):1163-70.

Iarussi et al., Protective effect of coenzyme Q10 on anthracyclines cardiotoxicity: control study in children with acute lymphoblastic leukemia and non-Hodgkin lymphoma. Mol Aspects Med. 1994;15 Suppl:s207-12.

Izyumov, Programmed Death of Cells and Oxidative Stress Caused by Inhibitors of Mitochondrial Functions. (synopsis of Ph.D. thesis), Moscow, 2005, pp. 17-20: URL: <http://www.lib.ua.net/diss/cont/151000.html>>.

Johnson et al., Gene expression profiles differentiate between sterile SIRS and early sepsis. Ann Surg. Apr. 2007;245(4):611-21.

Judy et al., Coenzyme Q10 Facts or Fiction. Natural Products Insider. 3 pages. Oct. 22, 2007.

Kawase et al., Enhancing effect of coenzyme, Q10 on immunorestoration with *Mycobacterium bovis* BCG in tumor-bearing mice. Gan. Aug. 1978;69(4):493-7.

Khan et al., Prolongation of Survival of Mice Bearing Leukemia 1210; Treated with Adriamycin and Coenzyme Q10. Proceedings of the American Association for Cancer Research. 1990;31:388, Poster 2303.

Kokawa et al., Coenzyme Q10 in cancer chemotherapy-experimental studies on augmentation of the effects of masked compounds, especially in the combined chemotherapy with immunopotentiators. Gan To Kagaku Ryoho. Mar. 1983;10(3):768-74. (Abstract only).

Kunitomo et al., Beneficial effect of coenzyme Q10 on increased oxidative and nitrative stress and inflammation and individual metabolic components developing in a rat model of metabolic syndrome. J Pharmacol Sci. Jun. 2008;107(2):128-37.

Lamson et al., Antioxidants in cancer therapy; their actions and interactions with oncologic therapies. Altern Med Rev. Oct. 1999;4(5):304-29.

Langer et al., Protein expression profiling in esophageal adenocarcinoma patients indicates association of heat-shock protein 27 expression and chemotherapy response. Clin Cancer Res. Dec. 15, 2008;14(24):8279-87.

Langham et al., Increased renal gene transcription of protein kinase C-beta in human diabetic nephropathy: relationship to long-term glycaemic control. Diabetologia. Apr. 2008;51(4):668-74.

Langsjoen, Alleviating Congestive Heart Failure with Coenzyme Q10. LifeExtension. http://www.lef.org/. Feb. 2008. 7 pages.

Laohapensang et al., An Unusual Complication of EVAR, Spontaneous Rectus Sheath Hematoma: A Case Report. Ann Vase Dis. 2009;2(2):122-5.

Larsson, Effects of isoprenoids on growth of normal human mammary epithelial cells and breast cancer cells in vitro. Anticancer Res. Jan.-Feb. 1994;14(1A):123-8.

Lassman, Molecular Biology of Gliomas. Current Neurology and Neuroscience Reports. 2004;4:228-233.

Li et al., Candidate genes responsible for human hepatocellular carcinoma identified from differentially expressed genes in hepatocarcinogenesis of the tree shrew (*Tupaia belangeri* chinesis). Hepatol Res. Jan. 2008;38(1):85-95.

Li et al., Protective Effect of Coenzyme Q10 against the Adverse Reaction of Mytomycin G in Mouse Liver. Acta Histochemica et Cytochemica. 1987;20(4):455-467.

Littman et al., Effect of Cholesterol-Free, Fat-Free Diet and Hypocholesteremic Agents on Growth of Transplantable Animal Tumors. Cancer Chemotherapy Reports. Jan.-Feb. 1966;50(1 and 2):25-45.

Lockwood et al., Apparent partial remission of breast cancer in 'high risk' patients supplemented with nutritional antioxidants, essential fatty acids and coenzyme Q10. Mol Aspects Med. 1994;15 Suppl:s231-40.

Lockwood et al., Partial and complete regression of breast cancer in patients in relation to dosage of coenzyme Q10. Biochem Biophys Res Commun. Mar. 30, 1994;199(3):1504-8.

Lockwood et al., Progress on therapy of breast cancer with vitamin Q10 and the regression of metastases. Biochem Biophys Res Commun. Jul. 6, 1995;212(1):172-7.

Mazoff, Bleeding Disorders & Hepatitis C. HCV Advocate, HCSP Fact Sheet. www.hcvadvocate.org. HCSP, Version 3, 5 pages. Dec. 2014.

Mazzio et al., Effects of enhancing mitochondrial oxidative phosphorylation with reducing equivalents and ubiquinone on 1-methyl-4-phenylpyridinium toxicity and complex I-IV damage in neuroblastoma cells. Biochem Pharmacol. Mar. 15, 2004;67(6):1167-84.

Merck Manual Japanese Edition, 17th ed., pp. 59-63 (2002).

(56) References Cited

OTHER PUBLICATIONS

Merlo et al., FOXP3 expression and overall survival in breast cancer. J Clin Oncol. Apr. 10, 2009;27(11):1746-52.

Miles et al., Coenzyme Q10 changes are associated with metabolic syndrome. Clin Chim Acta. Jun. 2004;344(1-2):173-9.

Modi et al., Effect of coenzyme Q10 on catalase activity and other antioxidant parameters in streptozotocin-induced diabetic rats. Biol Trace Elem Res. Jan. 2006;109(1):25-34.

Mohammed et al., Prognostic significance of vascular endothelial cell growth factors-A, -C and -D in breast cancer and their relationship with angio- and lymphangiogenesis. Br J Cancer. Apr. 10, 2007;96(7):1092-100.

Mousa, Antithrombotic Effects of Naturally Derived Products on Coagulation and Platelet Function. Anticoagulants, Antiplatelets, and Thrombolytics, 2nd Edition. Humana Press, 2010, Chapter 9, pp. 229-240.

Mura et al., Evaluation of transcutol as a clonazepam transdermal permeation enhancer from hydrophilic gel formulations. Eur J Pharm Sci. Feb. 2000;9(4):365-72.

Narain et al., API 31510 as a potential agent in management of CNS leukemia. Cancer Research. 2011;71 (Suppl 8), Abstract 1565. Proceedings: AACR 102nd Annual Meeting 2011.

Neidle, Cancer Drug Design and Discovery. Elsevier/Academic Press. p. 431, (2008).

NIH, National Cancer Institute, Continuous Infustion. Retrieved online at: https://www.cancer.gov/publications/dictionaries/cancer-terms/def/continuous-infusion. 1 page, (2020).

NIH, National Cancer Institute, Drugs Approved for Different Types of Cancer. 7 pages, Jan. 16, 2015.

Nissim, A Gentle Cancer Killer. University of Miami Medicine-Online. Retrieved online at: http://www6.miami.edu/ummedicine-magazine/fall2005/fstory4.html. 3 pages. 2005.

O'Driscoll et al., Feasibility and relevance of global expression profiling of gene transcripts in serum from breast cancer patients using whole genome microarrays and quantitative RT-PCR. Cancer Genomics Proteomics. Mar.-Apr. 2008;5(2):94-104.

Ohira et al., Expression profiling and characterization of 4200 genes cloned from primary neuroblastomas: identification of 305 genes differentially expressed between favorable and unfavorable subsets. Oncogene. Aug. 21, 2003;22(35):5525-36.

Okumura et al., Identification of biomarkers in ductal carcinoma in situ of the breast with microinvasion. BMC Cancer. Oct. 6, 2008;8:287.

Olopade et al., Overexpression of BCL-x protein in primary breast cancer is associated with high tumor grade and nodal metastases. Cancer J Sci Am. Jul.-Aug. 1997;3(4):230-7.

Olson, Karl August Folkers (1906-1997). American Society for Nutritional Sciences, J. Nutr. 2001;131:2227-2230.

Palan et al., Plasma concentrations of coenzyme Q10 and tocopherols in cervical intraepithelial neoplasia and cervical cancer. Eur J Cancer Prev. Aug. 2003;12(4):321-6.

Panwar et al., Preparation, characterization, and in vitro release study of albendazole-encapsulated nanosize liposomes. Int J Nanomedicine. Mar. 9, 2010;5:101-8.

Peddinghaus et al., Evaluation of the Usage Pattern and Safety Profile of a Frozen Plasma Transfusion Protocol. Transfusion. 2009;49:159A, Abstract SP285.

Persaud et al., Apoptotic affect of Ubiquinone precursors in melanoma. Cancer Research. Cellular and Molecular Biology. AACR Annual Meeting. 2 pages. Abstract 3281. May 1, 2009.

Perumal et al., Combined efficacy of tamoxifen and coenzyme Q10 on the status of lipid peroxidation and antioxidants in DMBA induced breast cancer. Mol Cell Biochem. May 2005;273(1-2):151-60.

Perumal et al., Therapeutic effect of tamoxifen and energy-modulating vitamins on carbohydrate-metabolizing enzymes in breast cancer. Cancer Chemother Pharmacol. 2005 ul;56(1):105-14.

Pfaffl et al., Real-time RT-PCR quantification of insulin-like growth factor (IGF)-1, IGF-1 receptor, IGF-2, IGF-2 receptor, insulin receptor, growth hormone receptor, IGF-binding proteins 1, 2 and 3 in the *Bovine* species. Domest Anim Endocrinol. Apr. 2002;22(2):91-102.

Pravst et al., Coenzyme Q10 contents in foods and fortification strategies. Crit Rev Food Sci Nutr. Apr. 2010;50(4):269-80.

Prostate-Specific Antigen (PSA) Test. Retrieved online at: http://www.cancer.gov/cancertopics/factsheet/detection /PSA. Mar. 18, 2009.

Rastogi, Analytical control of preservative labelling on skin creams. Contact Dermatitis. Dec. 2000;43(6):339-43. (Abstract only).

Riethdorf et al., Differential expression of CD66a (BGP), a cell adhesion molecule of the carcinoembryonic antigen family, in benign, premalignant, and malignant lesions of the human mammary gland. J Histochem Cytochem. Jul. 1997;45(7):957-63.

Roffe et al., Efficacy of coenzyme Q10 for improved tolerability of cancer treatments: a systematic review. J Clin Oncol. Nov. 1, 2004;22(21):4418-24.

Rydberg et al., Toll-like receptor agonists induce inflammation and cell death in a model of head and neck squamous cell carcinomas. Immunology. Sep. 2009;128(1 Suppl):e600-11.

Sander et al., Vesicle associated membrane protein (VAMP)-7 and VAMP-8, but not VAMP-2 or VAMP-3, are required for activation-induced degranulation of mature human mast cells. Eur J Immunol. Mar. 2008;38(3):855-63.

Scambia et al., Cathepsin D and epidermal growth factor in human breast cyst fluid. Br J Cancer. Nov. 1991;64(5):965-7.

Scotton et al., Analysis of CC chemokine and chemokine receptor expression in solid ovarian tumours. Br J Cancer. Sep. 14, 2001;85(6):891-7.

Seifried et al., The antioxidant conundrum in cancer. Cancer Res. Aug. 1, 2003;63(15):4295-8.

Shaoqiong et al., Related gene expressions in anti-keratinocyte aging induced by Ganoderma lucidum polysaccharides. J of Medical Colleges of PLA. 2008;23:167-175.

Shekelle et al., Effect of the supplemental use of antioxidants vitamin C, vitamin E, and coenzyme Q10 for the prevention and treatment of cancer. Evid Rep Technol Assess (Summ). Oct. 2003;(75):1-3.

Shen et al., Bioactive Components from the Mycelium of Antrodia salmonea. Journal of the Chinese Chemical Society. 2008;55:854-857.

Sheng et al., The efficacy of combining antiangiogenic agents with chemotherapy for patients with advanced non-small cell lung cancer who failed first-line chemotherapy: a systematic reviewand meta-analysis. PLoS One. Jun. 2, 2015;10(6):e0127306.

Shimada et al., Effect of high dose of pyridoxine on mammary tumorigenesis. Nutr Cancer. 2005;53(2):202-7.

Shimizu, Paclitaxel Pirarubicin Weekly. Japan J. Cancer and Chemotherapy, Jan. 2003;30:105-109.

Sieben et al., Differential Gene Expressionin Ovarian Tumors Reveals Dusp 4 and Serpina 5 as Key Regulators for Benign Behavior of Serous Borderline Tumors. J Clinical Oncology. Oct. 1, 2005;23(29):7275-7264.

Small Cell Lung Cancer Treatment (PDQ®)—National Cancer Institute. Retrieved online at: http://www.cancer.gov/cancertopics/pdq/treatment/small-cell-lung/healthprofessional. Jan. 20, 2012.

Soule et al., A human cell line from a pleural effusion derived from a breast carcinoma. J Natl Cancer Inst. Nov. 1973;51(5):1409-16.

The National Cancer Institute, Coenzyme Q10 (PDQ.RTM.) Patient Version. Retrieved online at: http://www.cancer.gov/cancertopics/pdq/cam/coenzymeQ10/patient/allpages. 13 pages, Jul. 10, 2009.

Thibault et al., Phase I Study of Lovastatin, an Inhibitor of the Mevalonate Pathway, in Patients with Cancer. Clinical Cancer Research. Mar. 1996;2:483-491.

Tockman et al., Considerations in bringing a cancer biomarker to clinical application. Cancer Res. May 1, 1992;52(9 Suppl):2711s-2718s.

Todaro et al., Apoptosis resistance in epithelial tumors is mediated by tumor-cell-derived interleukin-4. Cell Death Differ. Apr. 2008;15(4):762-72.

Tsubaki et al., [Investigation of the preventive effect of CoQ10 against the side-effects of anthracycline antineoplastic agents]. Gan To Kagaku Ryoho. Jul. 1984;11(7):1420-7.

(56) References Cited

OTHER PUBLICATIONS

Tsuneki et al., Coenzyme Q10 prevents high glucose-induced oxidative stress in human umbilical vein endothelial cells. Eur J Pharmacol. Jul. 2, 2007;566(1-3):1-10.
UT Health Cancer Center, Clinical trial to study the safety and efficacy of MBG453 given alone and in combination with PDR001 in adults with advanced cancer. Retrieved online at: http://www.uthscsa.edu/pateint-care/ctrc/clinical-trial/HSC20150730HU. 3 pages, Jul. 30, 2015.
Verhoeff et al., Bevacizumab and dose-intense temozolomide in recurrent high-grade glioma. Ann Oncol. Aug. 2010;21(8):1723-7.
Vermeer, Vitamin K: the effect on health beyond coagulation—an overview. Food & Nutrition Research. 2012;56(5329):1-6.
Women's Health Update: Coenzyme Q10 and Breast Cancer. Retrieved online at: http://www.encognitive.com/node/13574 on Dec. 26, 2012. 4 pages.
Yagasaki et al., Clinical significance of E-cadherin and vimentin co-expression in breast cancer. Int J Oncol. Oct. 1996;9(4):755-61.
Yang et al., Efficiency Observations of 116 cases on Coenzyme Q10 as an Auxiliary Therapy for Treating Diabetes Combined with Coronary Heart Disease. Journal of Chinese Physician. Oct. 2002;4(10):1148-1149.
Yunis et al., Human pancreatic carcinoma (MIA PaCa-2) in continuous culture: sensitivity to asparaginase. Int J Cancer. Jan. 1977;19(1):128-35.
Zhang et al., Preparation and Physico-chemical Property of Coenzyme Q10 Submicroemulsion. China Pharmacy. 2007;18(19):1476-1478.
Zhao et al., The Clinical Application of Coenzyme Q10. Shandong Medical Journal. Jan. 31, 1996;36(1):52.
Zucher et al., Liposome drugs' loading efficiency: a working model based on loading conditions and drug's physicochemical properties. J Control Release. Oct. 1, 2009;139(1):73-80.
European Search Report for Application No. EP10775420, dated Feb. 18, 2013. 7 pages.
International Preliminary Report on Patentability for Application No. PCT/US2014/033402, dated Oct. 13, 2014.
International Search Report and Written Opinion for Application No. PCT/US2010/034420, dated Feb. 7, 2011.
International Search Report and Written Opinion for Application No. PCT/US2017/043396, dated Oct. 6, 2017, 10 pages.
International Search Report for Application No. PCT/US2007/068052, dated Apr. 15, 2008.
International Search Report for Application No. PCT/US2008/057786, dated Oct. 23, 2008.
International Search Report for Application No. PCT/US2010/034376, dated Jan. 28, 2011. 3 pages.
International Search Report for Application No. PCT/US2010/034427, dated Jan. 17, 2011.
International Search Report for Application No. PCT/US2010/034447, dated Feb. 24, 2011, 4 pages.
International Search Report for Application No. PCT/US2010/034453, dated Jan. 31, 2011.
International Search Report for Application No. PCT/US2014/033402, dated Aug. 15, 2014.
Supplementary European Search Report for Application No. EP05711599, dated Apr. 10, 2008.
U.S. Appl. No. 10/597,378, filed Aug. 21, 2008, U.S. Pat. No. 8,147,825, Issued.
U.S. Appl. No. 13/410,085, filed Mar. 1, 2012, U.S. Pat. No. 8,293,227, Issued.
U.S. Appl. No. 13/791,313, filed Mar. 8, 2013, U.S. Pat. No. 8,586,030, Issued.
U.S. Appl. No. 13/366,224, filed Feb. 3, 2012, U.S. Pat. No. 8,562,976, Issued.
U.S. Appl. No. 14/031,706, filed Sep. 19, 2013, U.S. Pat. No. 8,771,680, Issued.
U.S. Appl. No. 14/282,336, filed May 20, 2014, 2014-0255372, Abandoned.
U.S. Appl. No. 16/900,162, filed Jun. 12, 2020, 2021-0128453, Published.
U.S. Appl. No. 13/439,615, filed Apr. 4, 2012, 2012-0269867, Abandoned.
U.S. Appl. No. 15/376,243, filed Dec. 12, 2016, U.S. Pat. No. 10,373,477, Issued.
U.S. Appl. No. 14/248,313, filed Apr. 8, 2014, 2014-0302014, Published.
U.S. Appl. No. 17/141,499, filed Jan. 5, 2021, Pending.
U.S. Appl. No. 13/9077,726, filed May 31, 2013, 2014-0017317, Abandoned.
U.S. Appl. No. 15/289,770, filed Oct. 10, 2016, 2017-0216223, Abandoned.
U.S. Appl. No. 17/321,699, filed May 17, 2021, Pending.
U.S. Appl. No. 14/477,828, filed Sep. 4, 2014, U.S. Pat. No. 9,901,542, Issued.
U.S. Appl. No. 15/869,630, filed Jan. 12, 2018, 2018-0353425, Published.
U.S. Appl. No. 15/656,986, filed Jul. 21, 2017, 2018-0021270, Published.
U.S. Appl. No. 17/376,357, filed Jul. 15, 2021, Pending.
U.S. Appl. No. 15/353,724, filed Nov. 16, 2016, 2017-0189350, Published.
U.S. Appl. No. 16/653,787, filed Oct. 15, 2019, 2020-0138744, Published.
U.S. Appl. No. 12/778,094, filed May 11, 2010, 2011-0027247, Abandoned.
U.S. Appl. No. 14/171,419, filed Feb. 3, 2014, U.S. Pat. No. 9,896,731, Issued.
U.S. Appl. No. 15/862,856, filed Jan. 5, 2018, U.S. Pat. No. 10,351,915, Issued.
U.S. Appl. No. 16/421,788, filed May 24, 2019, U.S. Pat. No. 11,028,446, Issued.
U.S. Appl. No. 17/232,795, filed Apr. 16, 2021, Pending.
U.S. Appl. No. 12/777,902, filed May 11, 2010, U.S. Pat. No. 10,519,504, Issued.
U.S. Appl. No. 12/778,029, filed May 11, 2010, U.S. Pat. No. 9,205,064, Issued.
U.S. Appl. No. 14/940,614, filed Nov. 13, 2015, 2016-0145693, Abandoned.
U.S. Appl. No. 15/841,972, filed Dec. 14, 2017, 2018-0334721, Abandoned.
U.S. Appl. No. 16/819,811, filed Mar. 19, 2020, Pending.
U.S. Appl. No. 12/778,054, filed May 11, 2010, 2011-0020312, Abandoned.
U.S. Appl. No. 12/778,010, filed May 11, 2010, 2011-0123986, Abandoned.
U.S. Appl. No. 15/011,196, filed Jan. 29, 2016, 2017-0137879, Abandoned.
U.S. Appl. No. 15/837,505, filed Dec. 11, 2017, 2019-0010554, Abandoned.
U.S. Appl. No. 16/456,257, filed Jun. 28, 2019, Abandoned.
U.S. Appl. No. 16/805,557, filed Feb. 28, 2020, 2021-0002725, Published.

* cited by examiner

METHOD OF TREATING OR PREVENTING TUMORS OF THE CENTRAL NERVOUS SYSTEM

CROSS REFERENCE TO RELATED APPLICATIONS

This application is a continuation application of U.S. patent application Ser. No. 15/376,243 filed Dec. 12, 2016, which, in turn, is a continuation application of U.S. patent application Ser. No. 13/439,615 filed Apr. 4, 2012, now abandoned, which, in turn, claims priority to U.S. Provisional Application Ser. No. 61/471,659, filed on Apr. 4, 2011. The applications are incorporated herein by reference in their entirety.

BACKGROUND

Central nervous system (CNS) tumors include tumors present in the brain, spinal cord, or the lining around such structures (e.g., meninges and Schwann cells) or eye. Tumors of the CNS may be categorized as primary CNS tumors or secondary CNS tumors. Primary CNS tumors are neoplasms that originate in the CNS. Secondary CNS tumors, the most common form of brain tumors, originate outside of the CNS and result from the primary tumor metastasizing to the CNS. Secondary CNS tumors can either involve the brain directly (i.e., parenchymal involvement) or involve the lining (i.e., leptomeningeal and meningeal involvement). In adults, solid tumors that have been shown to frequently metastasize to the CNS include lung, breast, adenocarcinoma of unknown primary site, melanoma, renal, and colon cancer. In children, primary solid tumors that more commonly metastasize to the CNS include sarcoma, Wilm's tumor, neuroblastoma, and germ cell tumor. In addition to solid tumors, haematological malignancies that can metastasize to the CNS include acute lymphoblastic leukemia, high grade non-Hodgkin's lymphoma, and less commonly acute myeloid leukemia.

Treatment of primary and secondary CNS tumors depends on the multiplicity, location, and grade of the tumor. Treatment of secondary CNS tumors may also depend upon the status of the systemic tumor. Treatment may include any of surgical resection, stereotactic radiosurgery (SRS), whole brain radiotherapy (WBRT) and chemotherapy or some combination thereof. Treatment of brain tumors faces a unique challenge compared to other types of cancers, due to the fact that not only are they developed within bone-covered structures, thereby having restricted space to expand, but they are also embedded deeply within an organ carrying a multitude of vital functions. Therefore, even a benign tumor can be life-threatening if it is in an area of the brain that controls critical body functions such as breathing or blood circulation. Treatment normally begins with surgical resection and then follows with radiation or chemotherapy. Surgery faces the risk of removing surrounding tissues that may carry vital brain functions, while radiation and chemotherapy can both harm normal tissues that are near or along the treatment path. Indeed, surgery usually is not recommended if the tumor is in regions of cerebral hemispheres that control speech, vision, movement or cognition. In addition, the use of radiation on children under the age of three is often prohibited because this is a critical time period of brain development. Efficacy of chemotherapy is somewhat limited due to frequent limited duration of effects and lack of targeting and selectivity of the drugs.

The inability of many conventional chemotherapeutic agents to cross the blood-brain barrier (BBB) has historically limited their use in the treatment of CNS tumors. The BBB is formed by the complex tight junctions between the endothelial cells of the brain capillaries and their low endocytic activity (Potschka et al., *Journal of Pharm. and Exp. Therapeutics* 306(1):124-131, 2003 July). This results in a capillary wall that behaves as a continuous lipid bilayer and prevents the passage of polar and lipid-insoluble substances. Additionally, ATP-dependent multidrug transporters such as P-glycoprotein (Pgp; ABCB1) and multidrug resistance protein MRP2 (ABCC2), which are found in the membranes of brain capillary endothelial cells, are thought to play an important role in BBB function by limiting drug penetration into the brain. It is, therefore, an obstacle to drugs that may combat diseases affecting the CNS.

SUMMARY OF THE INVENTION

The invention provides methods and compositions for treatment of a subject with a central nervous system (CNS) tumor comprising administration of a Coenzyme Q10 (CoQ10) compound, particularly when the subject exhibits at least one CNS abnormality as a result of the tumor.

The invention provides methods of treating a central nervous system (CNS) tumor in a subject exhibiting at least one CNS abnormality comprising administering to the subject a composition comprising a Coenzyme Q10 (CoQ10) compound, thereby treating the CNS tumor.

In certain embodiments, the CNS abnormality is one or more (e.g., 1, 2, 3, 4, 5, 6, 7, 8, 9, 10 or more) of a headache, a seizure, a change in memory especially loss of short term memory, a change in temperament, sudden onset of panic attacks induced by familiar situations, a change in intellectual function, inability to do math or find objects in plain sight; confusion, disorientation, becoming lost in a familiar location; blurred vision, loss of vision, loss of peripheral vision, double vision, dizziness, hearing problems, ringing in ears, buzzing in ears, seizure, decreased muscle control, lack of coordination, decreased sensation, weakness, paralysis, paraplegia, quadriplegia, difficulty with walking or change in gait, difficulty with speech, and balance problems. In certain embodiments, treatment results in amelioration of at least one CNS abnormality. In certain embodiments, at least one CNS abnormality comprises at least 2, at least 3, at least 4, at least 5, at least 6, at least 7, at least 8, at least 9, at least 10, at least 15, or at least 20 CNS abnormalities. In certain embodiments, at least one CNS abnormality comprises 2-10 CNS abnormalities, 3-10 CNS abnormalities, 4-10 CNS abnormalities, 5-10 CNS abnormalities, 5-15 CNS abnormalities, 6-15 CNS abnormalities, 7-15 CNS abnormalities, 8-20 CNS abnormalities, 10-20 CNS abnormalities.

In certain embodiments, the tumor is a primary tumor. In certain embodiments, the tumor is a metastatic tumor.

The invention provides methods of prevention or treatment of a secondary CNS tumor from a primary tumor in a subject comprising administering to the subject a composition comprising a Coenzyme Q10 (CoQ10) compound, thereby preventing or treating the secondary CNS tumor.

In certain embodiments, the primary tumor is a pediatric tumor. In certain embodiments, the pediatric tumor is a leukemia.

In certain embodiments, the primary tumor was treated with CNS radiation. In certain embodiments, the primary tumor was treated by administration of a chemotherapeutic agent to the CNS. In certain embodiments, administration of chemotherapy to the CNS comprises intrathecal administration of the chemotherapeutic agent.

In certain embodiments, the methods further comprise monitoring the subject for development of a secondary CNS tumor.

In certain embodiments, the subject is in remission for the primary tumor. In certain embodiments, the secondary tumor is identified at least one year after treatment is concluded. In certain embodiments, the secondary tumor is identified at least three years after treatment is concluded. In certain embodiments, the secondary tumor is identified at least five years after treatment is concluded. In certain embodiments, the secondary tumor is identified at least ten years after treatment is concluded.

In certain embodiments, the CoQ10 compound CoQ10.

In certain embodiments, the CNS tumor is in the subject at a location selected from the group consisting of brain, spinal cord, lining of the brain, lining of the spinal cord, and eye, or a combination thereof. In certain embodiments, the CNS tumor is a tumor selected from the group consisting of a tumor of neuroepithelial tissue, a tumor of cranial and paraspinal nerves, a tumor of the meninges, a tumor of the haematopoietic system, a germ cell tumor, a tumor of the sellar region, a lymphatic tumor, a leukemic tumor, a melanocytic tumor, a carcinoma tumor, and a sarcoma tumor.

In certain embodiments, the tumor is a leukemic tumor. In certain embodiments, the leukemic tumor is selected from the group consisting of chlorleukemic tumor, acute lymphoblastic leukemia (ALL) tumor, acute myelogenous leukemia (AML) tumor, acute promyelogenous leukemia tumor, and mixed lineage leukemia tumor.

In certain embodiments, the CoQ10 compound is administered orally.

In certain embodiments, the CoQ10 compound is administered topically.

In certain embodiments, the CoQ10 compound is administered parenterally.

In certain embodiments, the CoQ10 compound is administered by injection or infusion.

In certain embodiments, the CoQ10 compound is administered by a route selected from the group consisting of subcutaneously, intravenously, intramuscularly, intratumorally, intrathecally, intracranially, intraperitoneally, transcutaneously, intramedullaryly, intrathecally, intraventricularly, intraperitoneally, intraocularly, and intranasally.

In certain embodiments, the CoQ10 compound is not administered directly to the CNS. In certain embodiments, the CoQ10 compound is not administered intrathecally, intratumorally, intracranially, intramedullaryly, or intraocularly.

In certain embodiments, the methods further comprise administration of an additional agent. In certain embodiments, the additional agent is for treatment of the primary tumor or the secondary tumor. In certain embodiments, the agent for treatment of the primary tumor or the secondary tumor is a chemotherapeutic agent. In certain embodiments, the subject is further treated with radiation therapy. In certain embodiments, the subject is further treated with surgery.

In certain embodiments, the subject is human.

In certain embodiments, CoQ10 compound is administered at a dose of at least 50 mg/kg, at a dose of at least 75 mg/kg, at a dose of at least 100 mg/kg, at a dose of at least 125 mg/kg, at a dose of at least 150 mg/kg, at a dose of at least 200 mg/kg, at a dose of no more than 500 mg/kg, at a dose of no more than 400 mg/kg, at a dose of no more than 300 mg/kg.

In certain embodiments, the CoQ10 compound is administered three times per week. In certain embodiments, the CoQ10 compound is administered at least three times per week.

In certain embodiments, the CoQ10 compound is administered by intravenous infusion.

In certain embodiments, the CoQ10 compound is provided in an intravenous CoQ10 formulation comprising:
  an aqueous solution;
  a CoQ10 dispersed into a nano-dispersion of particles; and
  at least one of a dispersion stabilizing agent and an opsonization reducer;
  wherein the nano-dispersion of the CoQ10 is dispersed into nano-particles having a mean particle size of less than 200-nm.

In certain embodiments, the dispersion stabilizing agent is selected from the group consisting of pegylated castor oil, Cremophor EL, Cremophor RH 40, Pegylated vitamin E, Vitamin E TPGS, and Dimyristoylphosphatidyl choline (DMPC). In certain embodiments, the opsonization reducer is selected from the group consisting of poloxamers and poloxamines, e.g., poloxamer 188. In certain embodiments, the CoQ10 formulation has a weight-per-volume of the CoQ10, DMPC and poloxamer 188 of 4%, 3% and 1.5%, respectively.

In certain embodiments, the CoQ10 compound is administered topically.

In certain embodiments, the CoQ10 compound for topical administration is a 3% CoQ10 cream comprising:
  (1) a phase A having C12-15 alkyl benzoate at about 4.0% w/w of the composition, cetyl alcohol at about 2.00% w/w of the composition, stearyl alcohol at about 1.5% w/w, glyceryl stearate and PEG-100 at about 4.5% w/w;
  (2) a phase B having glycerin at about 2.00% w/w, propylene glycol at about 1.5% w/w, ethoxydiglycol at about 5.0% w/w, phenoxyethanol at about 0.475% w/w, a carbomer dispersion at about 40% w/w, purified water at about 16.7% w/w;
  (3) a phase C having triethanolamine at about 1.3% w/w, lactic acid at about 0.5% w/w, sodium lactate solution at about 2.0% w/w, water at about 2.5% w/w;
  (4) a phase D having titanium dioxide at about 1.0% w/w; and
  (5) a phase E having CoQ10 21% concentrate at about 15.0% w/w.

The invention provides compositions for practicing any of the methods provided herein.

The invention provides for the use of any of the compounds of claims provided herein for preparation of a medicament for use in the methods provided herein.

The invention provides composition for treating a central nervous system (CNS) tumor in a subject exhibiting at least one CNS abnormality the composition comprising a Coenzyme Q10 (CoQ10) compound, thereby treating the CNS tumor.

The invention provides compositions for preventing or treating of a secondary CNS tumor from a primary tumor in a subject the composition comprising a Coenzyme Q10 (CoQ10) compound, thereby preventing or treating the secondary CNS tumor.

BRIEF DESCRIPTION OF THE DRAWINGS

Various embodiments of the present disclosure will be described herein below with reference to the figures wherein.

DETAILED DESCRIPTION AND PREFERRED EMBODIMENTS

I. Definitions

Figures 1A, 1B:
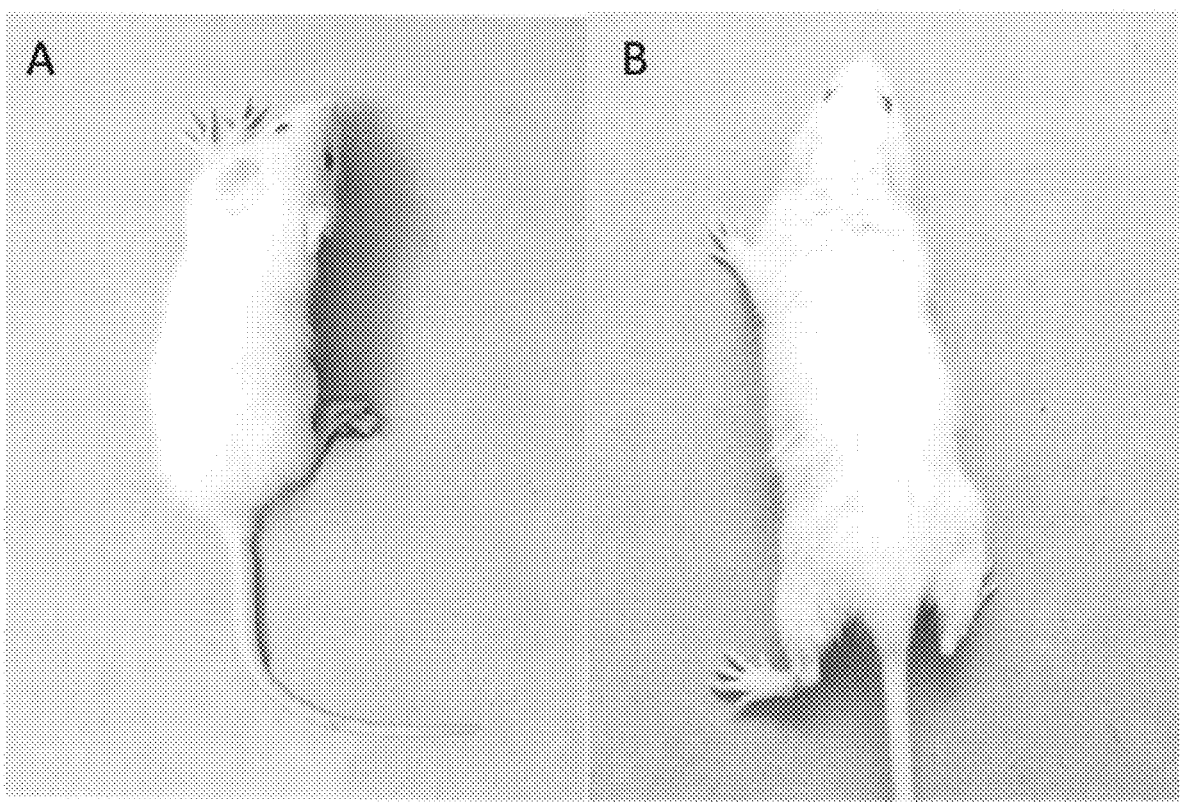
FIGS. 1A and 1B: Onset of paraplegia in Fischer 344 Rats. Development of paraplegia following treatment for leukemia with lipopolysaccharide (A), and the same animal following treatment with CoQ10 (B).

As used herein, a "central nervous system (CNS) tumor" is understood as a tumor present in at least one of the spinal cord, the brain, and the eye. The tumor may be a primary tumor, i.e. a tumor derived from a cell of the CNS. The tumor may be a metastatic tumor that originated at a remote site, i.e., a site outside of the CNS. A CNS tumor may also metastasize from one site in the CNS to another site within the CNS, e.g., from brain to spine. A CNS tumor can include one or more of a neuroepithelial tissue tumor, a tumor of cranial and/or paraspinal nerves, a tumor of the meninges, a tumor of the haematopoietic system, a germ cell tumor, a tumor of the sellar region, a lymphoma, a leukemia, a melanoma, a carcinoma, and a sarcoma tumor. Leukemic tumors include, for example, chloroleukemic tumors, acute lymphoblastic leukemia (ALL) tumors, acute myelogenous leukemia (AML) tumors, acute promyelogenous leukemia tumors, and mixed lineage leukemia tumors.

The terms "cancer" or "tumor" are well known in the art and refer to the presence, e.g., in a subject, of cells possessing characteristics typical of cancer-causing cells, such as uncontrolled proliferation, immortality, metastatic potential, rapid growth and proliferation rate, decreased cell death/ apoptosis, and certain characteristic morphological features. As used herein, the term "cancer" includes pre-malignant as well as malignant cancers.

As used herein, "cancer" refers to all types of cancer or neoplasm or malignant tumors found in humans, including, but not limited to: leukemias, lymphomas, melanomas, carcinomas and sarcomas. As used herein, the terms or language "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also cancer stem cells, as well as cancer progenitor cells or any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

As used herein, a "pediatric tumor" or "pediatric cancer" is a tumor or cancer first identified in a subject at or before the age of 18. Pediatric tumors include, but are not limited to, Ewing sarcoma, leukemia, neuroblastoma, osteosarcoma, rhabdomyosarcoma, soft tissue sarcoma, and Wilms' tumor.

A "central nervous system (CNS) abnormality" is understood as a sign or symptom of the presence of a CNS tumor that results in a change in behavior or physical well being of a subject as a result of the presence of the tumor. A subject may experience one or more CNS abnormalities as a result of a CNS tumor. The specific CNS abnormality will typically depend on, at least in part, the location, size, and type of CNS tumor. CNS abnormalities include, but are not limited to, headache, a seizure, a change in memory especially loss of short term memory, a change in temperament, e.g., sudden onset of panic attacks induced by familiar situations, a change in intellectual function, e.g., inability to do math or find objects in plain sight; confusion, disorientation, e.g., becoming lost in a familiar location; blurred vision, loss of vision, loss of peripheral vision, double vision, dizziness, hearing problems, ringing in ears, buzzing in ears, seizure, decreased muscle control, lack of coordination, decreased sensation, weakness, paralysis, e.g., paraplegia, quadriplegia, difficulty with walking or change in gait, difficulty with speech, and balance problems. As used herein, the CNS abnormality may be reported by anyone observing the subject, either directly or indirectly, e.g., the subject with the CNS abnormality him or herself, by a companion or caregiver of the subject with the CNS abnormality, or one of skill in the art. A CNS abnormality can include a physical abnormality detected by palpation or observed in an imaging study, e.g., by procedures such as CAT scan, MR imaging, X-ray, ultrasound, including an imaging study performed for a reason other than to detect the CNS abnormality. The CNS abnormalities need not be quantitatively or qualitatively analyzed as compared to a time prior to development of the CNS abnormality. As used herein, the CNS abnormality may be recognized by the subject prior to seeking treatment. In certain embodiments, the CNS abnormality is recognized after diagnosis of a CNS tumor by other methods (e.g., imaging study performed for reasons other than a CNS abnormality). In certain embodiments, the CNS tumor is detected when the subject seeks treatment for the CNS abnormality.

As used herein, the terms "treat," "treating" or "treatment" refer, preferably, to an action to obtain a beneficial or desired clinical result including, but not limited to, alleviation or amelioration of one or more signs or symptoms of a disease or condition, diminishing the extent of disease, stability (i.e., not worsening) state of disease, amelioration or palliation of the disease state, diminishing rate of or time to progression, and remission (whether partial or total), whether detectable or undetectable. "Treatment" of a cancer can also mean prolonging survival as compared to expected survival in the absence of treatment. Treatment need not be curative.

As used herein, "prevention of a secondary CNS tumor" is understood as delaying the onset, limiting the severity, or reducing the incidence of the development of a secondary CNS tumor in a subject suffering from or in a subject that has been treated for cancer, e.g., by prevention of extravasation of cancer cells into the CNS. In certain embodiments, the cancer is a leukemia, e.g., a chloroleukemia. In certain embodiment, the tumor is a pediatric tumor. The time to incidence and frequency of tumor metastasis to the CNS for various tumor types are known in the art.

As used herein, "amelioration of at least one CNS abnormality" is understood as the lessening in severity or frequency of one or more (e.g., at least 1, 2, 3, 4, 5, 6, 7, 8, 9, 10, etc.) CNS abnormality experienced by the subject as a result of treatment of the CNS tumor. Amelioration of at least one CNS abnormality can be understood as amelioration of 1-10, 2-10, 3-10, 4-10, 5-15, or more CNS abnormalities. Amelioration need not include complete elimination of signs or symptoms of the abnormality.

"Chemotherapeutic agent" is understood as a drug used for the treatment of cancer. Chemotherapeutic agents include, but are not limited to, small molecules and biologics (e.g., antibodies, peptide drugs, nucleic acid drugs).

A "therapeutically effective amount" is that amount sufficient to treat a disease in a subject. A therapeutically effective amount can be administered in one or more administrations.

The terms "administer", "administering" or "administration" include any method of delivery of a pharmaceutical composition or agent into a subject's system or to a particular region in or on a subject. In certain embodiments, the agent is delivered orally. In certain embodiments, the agent is administered parenterally. In certain embodiments, the agent is delivered by injection or infusion. In certain embodiments, the agent is delivered topically including transmucosally. In certain embodiments of the invention, an agent is administered by parenteral delivery, including, intravenous, intramuscular, subcutaneous, intramedullary injections, as well as intrathecal, direct intraventricular, intraperitoneal, intranasal, or intraocular injections. In one embodiment, the compositions provided herein may be administered by injecting directly to a tumor. In some embodiments, the formulations of the invention may be administered by intravenous injection or intravenous infusion. In certain embodiments, administration is systemic. In certain embodiments, administration is local. In some embodiments, one or more routes of administration may be combined, such as, for example, intravenous and intratumoral, or intravenous and peroral, or intravenous and oral, intravenous and topical, or intravenous and transdermal or transmucosal. In certain embodiments, the agent is not administered directly to the CNS, e.g., the agent is not delivered intrathecally, intratumorally, intracranially, intraventricularly, intramedullaryly, or intraocularly. Administering an agent can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery by a trained professional, e.g., intravenous delivery, intramuscular delivery, intratumoral delivery, etc.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, a "formulation" is understood as an active ingredient, e.g., CoQ10, a metabolite of CoQ10, a biosynthetic precursor of CoQ10, or a CoQ10 related compound, in combination with any pharmaceutically acceptable carrier. Formulations can include, but are not limited to, aqueous formulations, liposomal formulations, suspensions, emulsions, microemulsions, formulations for specific routes of administration, such as cream, lotion, and ointment formulations for topical administration, and solid formulations for oral administration.

As used herein, the term "safe and therapeutic effective amount" refers to the quantity of a component which is sufficient to yield a desired therapeutic response without undue adverse side effects (such as toxicity, irritation, or allergic response) commensurate with a reasonable benefit/risk ratio when used in the manner of this disclosure. By "therapeutically effective amount" is meant an amount of a compound of the present disclosure effective to yield the desired therapeutic response, e.g., amelioration of at least one sign or symptom of CNS tumor including amelioration of at least one CNS abnormality. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

"Therapeutically effective amount" means the amount of a compound that, when administered to a patient for treating a disease, is sufficient to effect such treatment for the disease. When administered for preventing a disease, the amount is sufficient to avoid or delay onset of the disease. The "therapeutically effective amount" will vary depending on the compound, the disease and its severity and the age, weight, etc., of the patient to be treated.

The term "therapeutic effect" refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically-effective amount of a compound will depend on its therapeutic index, solubility, and the like. For example, certain compounds discovered by the methods of the present invention may be administered in a sufficient amount to produce a reasonable benefit/risk ratio applicable to such treatment.

As used herein, "co-administration" or "combination therapy" is understood as administration of two or more active agents using separate formulations or a single pharmaceutical formulation, or consecutive administration in any order such that, there is a time period while both (or all) active agents simultaneously exert their biological activities. Co-administration does not require that the agents are administered at the same time, at the same frequency, or by the same route of administration. Examples of chemotherapeutic agents are provided herein.

As used herein, "co-administration" or "combination therapy" includes administration of a CoQ10 compound with one or more chemotherapeutic agent, or administration of two or more CoQ10 compounds.

As used herein, the term "survival" refers to the continuation of life of a subject which has been treated for a disease or condition, e.g., cancer. The time of survival can be defined from an arbitrary point such as time of entry into a clinical trial, time from completion or failure or an earlier treatment regimen, time from diagnosis, etc.

As used herein, the term "subject" refers to human and non-human animals, including veterinary subjects. The term "non-human animal" includes all vertebrates, e.g., mammals and non-mammals, such as non-human primates, mice, rabbits, sheep, dog, cat, horse, cow, chickens, amphibians, and reptiles. In a preferred embodiment, the subject is a human and may be referred to as a patient.

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of a listing of chemical group(s) in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

II. Coenzyme Q10 Compounds

CoEnzyme Q10 compounds are intended to include a class of CoQ10 compounds. Coenzyme Q10 compounds effective for the methods described herein include CoQ10, a metabolite of CoQ10, a biosynthetic precursor of CoQ10, an analog of CoQ10, a derivative of CoQ10, and CoQ10 related compounds. An analog of CoQ10 includes analogs having no or at least one isoprenyl repeats. CoQ10 has the following structure:

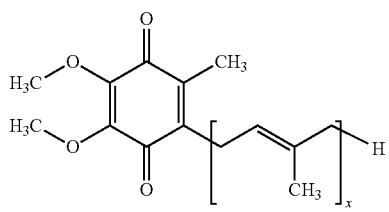

wherein x is 10. In the instant invention, CoQ10 can include derivatives of CoQ10 in which x is any number of isoprenyl units from 4-10, or any number of isoprenyl units from 6-10, or any number of isoprenyl units from 8-10, or 9-10 isoprenyl units. CoQ10 includes the fully oxidized version, also known as ubiquinone, the partially oxidized version, also known as semiquinone or ubisemiquinone, or the fully reduced version, also known as ubiquinol; or any mixtures or combinations thereof. In certain embodiments, the agent for treatment of a CNS tumor is ubiquinone. In certain embodiments, the agent for treatment of a CNS tumor is ubiquinols.

In certain embodiments of the present invention, the therapeutic agent is Coenzyme Q10 (CoQ10). Coenzyme Q10, also referred to herein as CoQ10, is also known as ubiquinone, or ubidecarenone. CoQ10 is art-recognized and further described in International Publication No. WO 2005/069916, the entire disclosure of which is incorporated by reference herein. CoQ10 is one of a series of polyprenyl 2,3-dimethoxy-5-methylbenzoquinone (ubiquinone) present in the mitochondrial electron transport systems of eukaryotic cells. Human cells produce CoQ10 exclusively and it is found in cell and mitochondrial membranes of all human cells, with the highest levels in organs with high energy requirements, such as the liver and the heart. The body pool of CoQ10 has been estimated to be about 2 grams, of which more than 50% is endogenous. Approximately 0.5 grams of CoQ10 is required from the diet or biosynthesis each day. CoQ10 is produced in ton quantities from the worldwide supplement market and can be obtained from Kaneka, with plants in Pasadena, Tex. and Takasagoshi, Japan.

Coenzyme Q10 related compounds include, but are not limited to, benzoquinones, isoprenoids, farnesols, farnesyl acetate, farnesyl pyrophosphate, 1-phenylalanine, d-phenylalanine, dl-phenylalanine, 1-tyrosine, d-tyrosine, dl-tyrosine, 4-hydroxy-phenylpyruvate, 4-hydroxy-phenyllactate, 4-hydroxy-cinnamate, dipeptides and tripeptides of tyrosine or phenylalanine, 3,4-dihydroxymandelate, 3-methoxy-4-hydroxyphenylglycol, 3-methoxy-4-hydroxymandelate, vanillic acid, phenylacetate, pyridoxine, S-adenosyl methionine, panthenol, mevalonic acid, isopentyl pyrophosphate, phenylbutyrate, 4-hydroxy-benzoate, decaprenyl pyrophosphate, beta-hydroxybutyrate, 3-hydroxy-3-methyl-glutarate, acetylcarnitine, acetoacetylcarnitine, acetylglycine, acetoacetylglycine, carnitine, acetic acid, pyruvic acid, 3-hydroxy-3-methylglutarylcarnitine, all isomeric forms of serine, alanine, cysteine, glycine, threonine, hydroxyproline, lysine, isoleucine, and leucine, even carbon number C4 to C8 fatty acids (butyric, caproic, caprylic, capric, lauric, myristic, palmitic, and stearic acids) salts of carnitine and glycine, e.g., palmitoylcarnitine and palmitoylglycine, and 4-hydroxy-benzoate polyprenyltransferase, any salts of these compounds, as well as any combinations thereof, and the like. In certain embodiments, such agents can be used for the treatment of a CNS tumor.

Metabolites and biosynthetic precursors of CoQ10 include, but are not limited to, those compounds that are formed between the chemical/biological conversion of tyrosine and acetyl-CoA to ubiquinol. Intermediates of the coenzyme biosynthesis pathway include tyrosine, acetyl-CoA, 3-hexaprenyl-4-hydroxybenzoate, 3-hexaprenyl-4,5-dihydroxybenzoate, 3-hexaprenyl-4-hydroxy-5-methoxy-benzoate, 2-hexaprenyl-6-methoxy-1,4-benzoquinone, 2-hexaprenyl-3-methyl-6-methoxy-1,4-benzoquinone, 2-hexaprenyl-3-methyl-5-hydroxy-6-methoxy-1,4-benzo-quinone, 3-Octaprenyl-4-hydroxybenzoate, 2-octaprenylphenol, 2-octaprenyl-6-methoxyphenol, 2-octaprenyl-3- methyl-6-methoxy-1,4-benzoquinone, 2-octaprenyl-3-methyl-5-hydroxy-6-methoxy-1,4-benzoquinone, 2-decaprenyl-3-methyl-5-hydroxy-6-methoxy-1,4-benzoquinone, 2-decaprenyl-3-methyl-6-methoxy-1,4-benzoquinone, 2-decaprenyl-6-methoxy-1,4-benzoquinone, 2-decaprenyl-6-methoxyphenol, 3-decaprenyl-4-hydroxy-5-methoxybenzoate, 3-decaprenyl-4,5-dihydroxybenzoate, 3-decaprenyl-4-hydroxybenzoate, 4-hydroxy phenylpyruvate, 4-hydroxyphenyllactate, 4-hydroxy-benzoate, 4-hydroxycinnamate, and hexaprenydiphosphate. In certain embodiments, such agents can be used for the treatment of a CNS tumor.

III. Compositions

The present disclosure provides compositions containing a CoQ10 compound for the treatment and prevention of cancer. The composition of the present disclosure can be administered to a patient either by themselves, or in pharmaceutical compositions where it is mixed with suitable carriers or excipient(s). In treating a patient exhibiting a disorder of interest, a therapeutically effective amount of an agent or agents such as these is administered. A therapeutically effective dose refers to that amount of the compound which results in amelioration of symptoms or a prolongation of survival in a patient.

Suitable routes of administration of the present compositions of the invention may include parenteral delivery, including, intravenous, intramuscular, subcutaneous, intramedullary injections, as well as intrathecal, direct intraventricular, intraperitoneal, intranasal, or intraocular injections, just to name a few. In one embodiment, the compositions provided herein may be administered by injecting directly to a tumor. In some embodiments, the formulations of the invention may be administered by intravenous injection or intravenous infusion. In one embodiment, the compositions of the invention are administered by intravenous injection. In one embodiment, the compositions of the invention are administered by intravenous infusion. Where the route of administration is, for example intravenous infusion, embodiments are provided herein where the IV infusion comprises the active agent, e.g., CoQ10, at approximately a 40 mg/mL concentration. Where the composition is administered by IV infusion, it can be diluted in a pharmaceutically acceptable aqueous solution such as phosphate buffered saline or normal saline. In some embodiments, one or more routes of administration may be combined, such as, for example, intravenous and intratumoral, or intravenous and peroral, or intravenous and oral, or intravenous and topical, transdermal, or transmucosal.

The compositions described herein may be administered to a subject in any suitable formulation. These include, for example, liquid, semi-solid, and solid dosage forms, such as liquid solutions (e.g., injectable and infusible solutions), dispersions or suspensions, tablets, pills, powders, creams, lotions, liniments, ointments, or pastes, drops for administration to the eye, ear or nose, liposomes, and suppositories. The preferred form depends on the intended mode of administration and therapeutic application.

In certain embodiments, a CoQ10 compound may be prepared with a carrier that will protect against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

For example, a CoQ10 compound can be formulated for parenteral delivery, e.g., for subcutaneous, intravenous, intramuscular, or intratumoral injection. The compositions may be administered in a single bolus, multiple injections, or by continuous infusion (for example, intravenously or by peritoneal dialysis). For parenteral administration, the compositions may be formulated in a sterilized pyrogen-free form.

Use of pharmaceutically acceptable carriers to formulate the compounds herein disclosed, for the practice of the present invention, into dosages suitable for systemic administration is within the scope of the present disclosure. With proper choice of carrier and suitable manufacturing practice, the compositions of the present disclosure, in particular, those formulated as solutions, may be administered parenterally, such as by intravenous injection.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices may be desirable. The data obtained from these cell culture assays and animal studies can be used in formulating a range of dosage for use in human. The dosage of such compounds may be within a range of circulating concentrations that include the ED50 with little or no toxicity. The dosage may vary within this range depending upon the dosage form employed and the route of administration utilized.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers including excipients and auxiliaries which facilitate processing of the active compounds into preparations which can be used pharmaceutically. The preparations formulated for intravenous administration may be in the form of solutions of colloidal dispersion.

Pharmaceutical compositions for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

IV. Formulations

The active agent, e.g., a CoQ10 compound, can be delivered in any pharmaceutically acceptable carrier for the desired route of administration. As used herein, formulations including CoQ10 compounds are formulated for any route of administration unless otherwise clearly indicated. In preferred embodiments, the formulations are for administration by injection, infusion, or topical administration.

Preferred therapeutic formulations for use in the methods of the invention comprise the active agent (e.g., a CoQ10 compound) in a microparticle formation, e.g., for intravenous administration. Such intravenous formulations are provided, for example, in WO2011/112900 which is incorporated herein in its entirety by reference and an intravenous formulation is used in the examples set forth below. Through high pressure homogenization, active agent (e.g., a CoQ10 compound) particles are reduced to produce particles that are small enough to pass through a 200-nm sterilizing filter. Particles that are small enough to pass through a 200-nm sterilizing filter can be injected intravenously. These particles are much smaller than blood cells and therefore will not embolize capillaries. Red blood cells for example are 6-micron×2-micron disks. The particles are dispersed to and are encased or surrounded by a stabilizing agent. While not wishing to be bound by any theory, it is believed that the stabilizing agents are attracted to the hydrophobic therapeutic agent such that the dispersed particles of the hydrophobic therapeutic agent are surrounded by the stabilizing agent forming a suspension or an emulsion. The dispersed particles in the suspension or emulsion comprises a stabilizing agent surface and a core consisting of the hydrophobic therapeutic agent, e.g., a CoQ10 compound, in a solid particulate form (suspension) or in an immiscible liquid form (emulsion). The dispersed particles can be entrenched in the lipophilic regions of a liposome.

Dispersed colloidal systems permit a high drug load in the formulation without the use of co-solvents. Additionally, high and relatively reproducible plasma levels are achieved without the dependence on endogenous low-density lipoprotein carriers. More importantly, the formulations allow sustained high drug levels in solid tumors due to the passive accumulation of the colloidal particles of the hydrophobic therapeutic agent.

A preferred intravenous formulation substantially comprises a continuous phase of water and dispersed solids (suspension) or dispersed immiscible liquid (emulsion). Dispersed colloidal systems, in which the particles are composed largely of the active agent (drug) itself, can often deliver more drug per unit volume than continuous solubilizing systems, if the system can be made adequately stable.

As the formulation medium, the aqueous solution may include Hank's solution, ringer's solution, phosphate buffered saline (PBS), physiological saline buffer or other suitable salts or combinations to achieve the appropriate pH and osmolarity for parenterally delivered formulations. The aqueous solution may contain substances which increase the viscosity of the solution, such as sodium carboxymethyl cellulose, sorbitol, or dextran.

The active agent (e.g., a CoQ10 compound) is dispersed in the aqueous solution such that a colloidal dispersion is formed wherein the nano-dispersion particles of the hydrophobic therapeutic agent are covered or encased or encircled by the dispersion stabilizing agents to form nano-dispersions of the active agent (e.g., a CoQ10 compound) particles. The nano-dispersed active agent (e.g., a CoQ10 compound) particles have a core formed of the hydrophobic therapeutic agent that is surrounded by the stabilizing agent. Similarly, in certain aspects, the stabilizing agent is a phospholipid having both a hydrophilic and lipophilic portion. The phospholipids form liposomes or other nanoparticles upon homogenization. In certain aspects these liposomes are bi-layered unilamellar liposomes while in other embodiments the liposomes are bi-layered multi-lamellar liposomes. The dispersed active agent (e.g., a CoQ10 compound) particles are dispersed in the lipophilic portion of the bi-layered structure of the liposome formed from the phospholipids. In certain other aspects the core of the liposome, like the core of the nano-dispersion of active agent (e.g., a CoQ10 compound) particles, is formed of the hydrophobic therapeutic agent and the outer layer is formed of the bi-layered structure of the phospholipid. In certain embodiments the colloidal dispersions are treated by a lyophilization process whereby the nanoparticle dispersion is converted to a dry powder.

In some embodiments, the formulation for injection or infusion used is a 4% sterile aqueous colloidal dispersion containing CoQ10 in a nanosuspension as prepared in WO2011/112900. In certain embodiments, the formulation includes an aqueous solution; a hydrophobic active agent, e.g., CoQ10, a CoQ10 precursor or metabolite or a CoQ10 related compound, dispersed to form a colloidal nano-dispersion of particles; and at least one of a dispersion stabilizing agent and an opsonization reducer; wherein the colloidal nano-dispersion of the active agent is dispersed into nano-dispersion particles having a mean size of less than 200-nm.

In certain embodiments, the dispersion stabilizing agent includes, but is not limited to, pegylated castor oil, Cremphor EL, Cremophor RH 40, Pegylated vitamin E, Vitamin E TPGS, and Dimyristoylphosphatidyl choline (DMPC).

In certain embodiments, the opsonization reducer is a poloxamer or a poloxamines.

In certain embodiments, the colloidal nano-dispersion is a suspension or an emulsion, optionally, a colloidal nano-dispersion is in a crystalline form or a super-cooled melt form.

In certain embodiments, the formulation includes a lyoprotectant such as a nutritive sugar including, but not limited to, lactose, mannose, maltose, galactose, fructose, sorbose, raffinose, neuraminic acid, glucosamine, galactosamine, N-methylglucosamine, mannitol, sorbitol, arginine, glycine and sucrose, or any combination thereof.

In certain embodiments, the injectable formulation includes an aqueous solution; a hydrophobic active agent dispersed to form a colloidal nano-dispersion of particles; and at least one of a dispersion stabilizing agent and an opsonization reducer. The colloidal nano-dispersion of the active agent is dispersed into nano-dispersion particles having sizes of less than 200-nm. In some embodiments the dispersion stabilizing agent is selected from natural or semisynthetic phospholipids. For example, suitable stabilizing agents include polyethoxylated (a/k/a pegylated) castor oil (Cremophor® EL), polyethoxylated hydrogenated castor oil (Cremophor® RH 40), Tocopherol polyethylene glycol succinate (Pegylated vitamin E, Vitamin E TPGS), Sorbitan fatty acid esters (Spans®), Bile acids and bile-acid salts or Dimyristoylphosphatidyl choline (DMPC). In some embodiments the stabilizing agent is DMPC.

In certain embodiments the formulation is suitable for parenteral administration, including intravenous, intraperitoneal, orthotopical, intracranial, intramuscular, subcutaneous, intramedullary injections, as well as intrathecal, direct intraventricular, intranasal, or intraocular injections. In certain embodiments, the formulation contains CoQ10, dimyristoyl-phophatidylcholine, and poloxamer 188 in a ratio of 4:3:1.5 respectively that is designed to stabilize the nanosuspension of the particles. In some embodiments, the formulation includes a phosphate buffer saline solution which contains sodium phosphate dibasic, potassium phosphate monobasic, potassium chloride, sodium chloride and water for injection. In certain embodiments, the 4% sterile aqueous colloidal dispersion containing CoQ10 in a nano-suspension is diluted in the phosphate buffered saline solution provided, e.g., 1:1, 1:2, 1:3, 1:4. 1:5, 1:6, 1:7, 1:8. 1:9, 1:10, 1:11, 1:12, 1:13, 1:14. 1:15, 1:16, 1:17, 1:18. 1:19, 1:20, or other appropriate ratio bracketed by any two of the values.

In some embodiments, the formulation is a topical formulation. Topical formulations of CoQ10 compounds are provided, for example in WO2010/132507, WO2009/126764, WO2008116135, and WO2005/069916, the entire contents of each are expressly incorporated herein.

Formulations suitable for topical administration include liquid or semi-liquid preparations suitable for penetration through the skin, such as liniments, lotions, creams, ointments or pastes, and drops suitable for administration to the eye, ear, or nose. Drops according to the present disclosure may include sterile aqueous or oily solutions or suspensions and may be prepared by dissolving the active ingredient in a suitable aqueous solution of a bactericidal and/or fungicidal agent and/or any other suitable preservative, and in some embodiments including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present disclosure include those suitable for application to the skin or eye. An eye lotion may include a sterile aqueous solution optionally containing a bactericide and may be prepared by methods similar to those for the preparation of drops. Lotions or liniments for application to the skin may also include an agent to hasten drying and to cool the skin, such as an alcohol, and/or a moisturizer such as glycerol or an oil such as castor oil or arachis oil.

Creams, ointments or pastes useful in the methods of the invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may include hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

In some embodiments, the remaining component of a topical delivery vehicle may be water or a water phase, in embodiments purified, e.g. deionized, water, glycerine, propylene glycol, ethoxydiglycol, phenoxyethanol, and cross linked acrylic acid polymers. Such delivery vehicle compositions may contain water or a water phase in an amount from about 50 to about 95 percent, based on the total weight of the composition. The specific amount of water present is not critical, however, being adjustable to obtain the desired viscosity (usually about 50 cps to about 10,000 cps) and/or concentration of the other components. The topical delivery vehicle may have a viscosity of at least about 30 centipoises.

Topical formulations can also include an oil phase including, for example, oil phase which, in turn, may include emollients, fatty alcohols, emulsifiers, combinations thereof, and the like. For example, an oil phase could include emollients such as C12-15 alkyl benzoates (commercially available as FINSOLV™ TN from Finetex Inc. (Edison, N.J.)), capric-caprylic triglycerides (commercially available from Huls as MIGLYOL™ 812), and the like. Other suitable emollients which may be utilized include vegetable derived oils (corn oil, safflower oil, olive oil, macadamian nut oil, etc.); various synthetic esters, including caprates, linoleates, dilinoleates, isostearates, fumarates, sebacates, lactates, citrates, stearates, palmitates, and the like; synthetic medium chain triglycerides, silicone oils or polymers; fatty alcohols such as cetyl alcohol, stearyl alcohol, cetearyl alcohol, lauryl alcohol, combinations thereof, and the like; and emulsifiers including glyceryl stearate, PEG-100 stearate, Glyceryl Stearate, Glyceryl Stearate SE, neutralized or partially neutralized fatty acids, including stearic, palmitic, oleic, and the like; vegetable oil extracts containing fatty acids, Ceteareth-20, Ceteth-20, PEG-150 Stearate, PEG-8 Laurate, PEG-8 Oleate, PEG-8 Stearate, PEG-20 Stearate, PEG-40 Stearate, PEG-150 Distearate, PEG-8 Distearate, combinations thereof, and the like; or other non-polar cosmetic or pharmaceutically acceptable materials used for skin emolliency within the purview of those skilled in the art, combinations thereof, and the like.

Topical formulations can also include a liposomal concentrate including, for example, a phospholipid such as lecithin, lysolecithin, phosphatidylcholine, phosphatidylethanolamine, phosphatidylinositol, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, and combinations thereof, at least one lipophilic bioactive agent, and at least one solubilizer. The liposomal concentrate may be in combination with at least one pharmaceutically acceptable carrier possessing at least one permeation enhancer in an amount from about 0.5% by weight to about 20% by weight of the composition. The phospholipid may present in the composition in an amount from about 2% to about 20% by weight of the composition and the bioactive agent may be present in an amount from about 0.5% to about 20% by weight of the composition.

Transdermal skin penetration enhancers can also be used to facilitate delivery of CoQ10. Illustrative are sulfoxides such as ethoxydiglycol, 1,3-butylene glycol, isopentyl diol, 1,2-pentane diol, propylene glycol, 2-methyl propan-2-ol, propan-2-ol, ethyl-2-hydroxypropanoate, hexan-2,5-diol, di(2-hydroxypropyl)ether, pentan-2,4-diol, acetone, polyoxyethylene(2)methyl ether, 2-hydroxypropionic acid, 2-hydroxyoctanoic acid, propan-1-ol, 1,4 dioxane, tetrahydrofuran, butan-1,4-diol, propylene glycol dipelargonate, polyoxypropylene 15 stearyl ether, octyl alcohol, polyoxyethylene ester of oleyl alcohol, oleyl alcohol, lauryl alcohol, dioctyl adipate, dicapryl adipate, diisopropyl adipate, diisopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, isopropyl palmitate, ethyl laurate, 2-ethyl-hexyl pelargonate, isopropyl isostearate, butyl laurate, benzyl benzoate, butyl benzoate, hexyl laurate, ethyl caprate, ethyl caprylate, butyl stearate, benzyl salicylate, 2-hydroxyoctanoic acid, dimethyl sulphoxide, methyl sulfonyl methane, n,n-dimethyl acetamide, n,n-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, 1-dodecylazacycloheptan-2-one, and combinations thereof.

Solubilizers, particularly for topical administration can include, but are not limited to, polyoxyalkylene dextrans, fatty acid esters of saccharose, fatty alcohol ethers of oligoglucosides, fatty acid esters of glycerol, fatty acid esters of polyoxyethylenes, polyethoxylated fatty acid esters of sorbitan, fatty acid esters of poly(ethylene oxide), fatty alcohol ethers of poly(ethylene oxide), alkylphenol ethers of poly(ethylene oxide), polyoxyethylene-polyoxypropylene block copolymers, ethoxylated oils, and combinations thereof.

Topical formulations can include emollients, including, but not limited to, C12-15 alkyl benzoates, capric-caprylic triglycerides, vegetable derived oils, caprates, linoleates, dilinoleates, isostearates, fumarates, sebacates, lactates, citrates, stearates, palmitates, synthetic medium chain triglycerides, silicone oils, polymers and combinations thereof; the fatty alcohol is selected from the group consisting of cetyl alcohol, stearyl alcohol, cetearyl alcohol, lauryl alcohol and combinations thereof; and the emulsifier is selected from the group consisting of glyceryl stearate, polyethylene glycol 100 stearate, neutralized fatty acids, partially neutralized fatty acids, polyethylene glycol 150 stearate, polyethylene glycol 8 laurate, polyethylene glycol oleate, polyethylene glycol 8 stearate, polyethylene glycol 20 stearate, polyethylene glycol 40 stearate, polyethylene glycol 150 distearate, polyethylene glycol 8 distearate, and combinations thereof.

Topical formulations can include a neutralization phase comprising one or more of water, amines, sodium lactate, and lactic acid.

The water phase can further optionally include one or more of water phase comprises the permeation enhancer optionally in combination with a viscosity modifier selected from the group consisting of cross linked acrylic acid polymers, pullulan, mannan, scleroglucans, polyvinylpyrrolidone, polyvinyl alcohol, guar gum, hydroxypropyl guar gum, xanthan gum, acacia gum, arabia gum, tragacanth, galactan, carob gum, karaya gum, locust bean gum, carrageenin, pectin, amylopectin, agar, quince seed, rice starch, corn starch, potato starch, wheat starch, algae extract, dextran, succinoglucan, carboxymethyl starch, methylhydroxypropyl starch, sodium alginate, alginic acid propylene glycol esters, sodium polyacrylate, polyethylacrylate, polyacrylamide, polyethyleneimine, bentonite, aluminum magnesium silicate, laponite, hectonite, and anhydrous silicic acid.

Topical formulations can also include a pigment such as titanium dioxide.

In an embodiment, a topical formulation for use in the methods of the invention includes an oil phase comprising C12-15 alkyl benzoates, cetyl alcohol, stearyl alcohol, glyceryl stearate, and polyethylene glycol 100 stearate, in an amount of from about 5% to about 20% by weight of the composition; a water phase comprising glycerin, propylene glycol, ethoxydiglycol, phenoxyethanol, water, and a cross-linked acrylic acid polymer, in an amount of from about 60 to about 80% by weight of the composition; a neutralization phase comprising water, triethanolamine, sodium lactate, and lactic acid, in an amount of from about 0.1% to about 15% by weight of the composition; a pigment comprising titanium dioxide in an amount of from about 0.2% to about 2% by weight of the composition; and a liposomal concentrate comprising a polyethoxylated fatty acid ester of sorbitan, coenzyme Q10, a phosphatidylcholine lecithin, phenoxyethanol, propylene glycol, and water, in an amount of from about 0.1% to about 30% by weight of the composition, wherein the propylene glycol and ethoxydiglycol are present in a combined amount of from 3% by weight to about 15% by weight of the composition and the coenzyme Q10 is present in an amount of from about 0.75% by weight to about 10% by weight of the composition. Other formulations for use in the methods of the invention are provided, for example, in WO2008/116135 which is incorporated herein by reference.

In some embodiments, a formulation for any route of administration for use in the invention may include from about 0.001% to about 20% (w/w) of CoQ10, more preferably between about 0.01% and about 15% and even more preferably between about 0.1% to about 10% (w/w) of CoQ10. In one embodiment a formulation includes about 4% (w/w) of CoQ10. In one embodiment a formulation includes about 8% (w/w) of CoQ10. In various embodiments, the formulation includes about 0.1%, 0.2%, 0.3%, 0.4%, 0.5%, 1%, 2%, 3%, 4%, 5%, 6%, 7%, 8%, 9%, 10%, 11%, 12%, 13%, 14%, 15%, 16%, 17%, 18%, 19% or 20% (w/w) of CoQ10, or any range bracketed by any two values recited. CoQ10 can be obtained from Kaneka Q10 as Kaneka Q10 (USP UBIDECARENONE) in powdered form (Pasadena, Tex., USA). CoQ10 used in the methods exemplified herein have the following characteristics: residual solvents meet USP 467 requirement; water content is less than 0.0%, less than 0.05% or less than 0.2%; residue on ignition is 0.0%, less than 0.05%, or less than 0.2% less than; heavy metal content is less than 0.002%, or less than 0.001%; purity of between 98-100% or 99.9%, or 99.5%.

In certain embodiments, the concentration of CoQ10 in the formulation is between 1 mg/mL and 150 mg/mL. In one embodiment, the concentration of CoQ10 in the formulation is between 5 mg/mL and 125 mg/mL. In one embodiment, the concentration of CoQ10 in the formulation is between 10 mg/mL and 100 mg/mL. In one embodiment, the concentration of CoQ10 in the formulation is between 20 mg/mL and 90 mg/mL. In one embodiment, the concentration of CoQ10 is between 30 mg/mL and 80 mg/mL. In one embodiment, the concentration of CoQ10 is between 30 mg/mL and 70 mg/mL. In one embodiment, the concentration of CoQ10 is between 30 mg/mL and 60 mg/mL. In one embodiment, the concentration of CoQ10 is between 30 mg/mL and 50 mg/mL. In one embodiment, the concentration of CoQ10 is between 35 mg/mL and 45 mg/mL. It should be understood that additional ranges having any one of the foregoing values as the upper or lower limits are also intended to be part of this invention, e.g., between 10 mg/mL and 50 mg/mL, or between 20 mg/mL and 60 mg/mL.

In certain embodiments, the concentration of CoQ10 in the formulation is about 10, 15, 20, 25, 30, 31, 32, 33, 34, 35, 36, 37, 38, 39, 40, 41, 42, 43, 44, 45, 46, 47, 48, 49, 50, 55, 60, 65, 70, 75, 80, 85, 90 or 95 mg/mL. In one embodiment, the concentration of CoQ10 in the formulation is about 50 mg/mL. In one embodiment, the concentration of CoQ10 in the formulation is about 60 mg/mL. In one embodiment, the concentration of CoQ10 in the formulation is about 30 mg/mL. In a preferred embodiment, the concentration of CoQ10 in the formulation is about 40 mg/mL. It should be understood that ranges having any one of these values as the upper or lower limits are also intended to be part of this invention, e.g. between 37 mg/mL and 47 mg/mL, or between 31 mg/mL and 49 mg/mL.

It is understood that formulations can similarly be prepared containing CoQ10 precursors, metabolites, and related compounds.

V. Treatment of Cancer

Formulations of the present disclosure may be utilized for the treatment of cancer including primary and secondary tumors. Accordingly, the present invention provides methods of treating or preventing cancer in a subject, comprising administering the formulations of the invention to the subject in an amount sufficient to treat or prevent the cancer, thereby treating or preventing cancer. The formulations of the invention may also be utilized for inhibiting tumor cell growth. Accordingly, the invention further provides methods of inhibiting tumor cell growth in a subject, comprising administering the formulations of the invention to the subject, such that tumor cell growth is inhibited. The invention also provides embodiments in which the formulation is administered to the subject by a route other than direct administration to the CNS, i.e., not intrathecally, intracranially, intraventricularly, intramedullaryly, or intraocularly. In certain embodiments, the agent is not administered into the CNS tumor. In certain embodiments, the subject is a human subject.

Such formulations may include the hydrophobic therapeutic agent, e.g., CoQ10, its metabolites, or CoQ10 related compounds, in a pharmaceutically acceptable carrier. In some embodiments, such a formulation may include from about 0.001% to about 20% (w/w) of CoQ10, more preferably between about 0.01% and about 15% and even more preferably between about 0.1% to about 10% (w/w) of CoQ10. In one embodiment a formulation includes about 4% (w/w) of CoQ10. In one embodiment a formulation includes about 8% (w/w) of CoQ10. In various embodiments, the formulation includes about 0.1%, 0.2%. 0.3%, 0.4%. 0.5%, 0.6%, 0.7%, 0.8%. 0.9%, 1%, 2%, 3%, 4%, 5%, 6%, 7%, 8%, 9%, 10%, 11%, 12%, 13%, 14%, 15%, 16%, 17%, 18%, 19% or 20% (w/w) of CoQ10, or any range bracketed by those values. As also noted herein, compositions of the present disclosure may be in a liquid form, capable of introduction into a subject by any means or route of administration within the purview of those skilled in the art. For example, compositions may be administered by routes of administration including, but not limited to, intravenous, intratumoral, combinations thereof, and the like.

In certain embodiments of the invention, methods are provided for treating or preventing cancer in a human by intravenously administering a CoQ10, CoQ10 precursor, metabolite, or related compound formulation to the human such that treatment or prevention occurs, wherein the human is administered a dose of the formulation such that, preferably, CoQ10 is administered in the range of about 0.5 mg/kg to about 10,000 mg/kg, about 5 mg/kg to about 5,000 mg/kg, about 10 mg/kg to about 3,000 mg/kg. In one embodiment, the formulation is administered such that, preferably, CoQ10 is administered in the range of about 10 mg/kg to about 1,400 mg/kg. In one embodiment, the formulation is administered such that, preferably, CoQ10 is administered in the range of about 10 mg/kg to about 650 mg/kg. In one embodiment, the formulation is administered such that, preferably, CoQ10 is administered in the range of about 10 mg/kg to about 200 mg/kg. In various embodiments, the formulation is administered such that, preferably, CoQ10 is administered at a dose of about 2 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 56 mg/kg, 57 mg/kg, 58 mg/kg, 59 mg/kg, 60 mg/kg, 65 mg/kg, 70 mg/kg, 75 mg/kg, 76 mg/kg, 77 mg/kg, 78 mg/kg, 79 mg/kg, 80 mg/kg, 85 mg/kg, 90 mg/kg, 95 mg/kg, 100 mg/kg, 101 mg/kg, 102 mg/kg, 103 mg/kg, 104 mg/kg, 105 mg/kg, 106 mg/kg, 107 mg/kg, 108 mg/kg, 109 mg/kg, 110 mg/kg, 120 mg/kg, 130 mg/kg, 140 mg/kg, 150 mg/kg, 160 mg/kg, 170 mg/kg, 180 mg/kg, 190 mg/kg or 200 mg/kg. In various embodiments, the formulation is administered such that, preferably, CoQ10 is administered at a dose of at least 2 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 56 mg/kg, 57 mg/kg, 58 mg/kg, 59 mg/kg, 60 mg/kg, 65 mg/kg, 70 mg/kg, 75 mg/kg, 76 mg/kg, 77 mg/kg, 78 mg/kg, 79 mg/kg, 80 mg/kg, 85 mg/kg, 90 mg/kg, 95 mg/kg, 100 mg/kg, 101 mg/kg, 102 mg/kg, 103 mg/kg, 104 mg/kg, 105 mg/kg, 106 mg/kg, 107 mg/kg, 108 mg/kg, 109 mg/kg, 110 mg/kg, 120 mg/kg, 130 mg/kg, 140 mg/kg, 150 mg/kg, 160 mg/kg, 170 mg/kg, 180 mg/kg, 190 mg/kg or 200 mg/kg, wherein the dose does not result in any limiting toxicities. It should be understood that ranges having any one of these values as the upper or lower limits are also intended to be part of this invention, e.g., about 50 mg/kg to about 200 mg/kg, or about 650 mg/kg to about 1400 mg/kg, or about 55 mg/kg to about 110 mg/kg. In one embodiment the administered dose is at least about 1 mg/kg, at least about 5 mg/kg, at least about 10 mg/kg, at least about 12.5 mg/kg, at least about 20 mg/kg, at least about 25 mg/kg, at least about 30 mg/kg, at least about 35 mg/kg, at least about 40 mg/kg, at least about 45 mg/kg, at least about 50 mg/kg, at least about 55 mg/kg, at least about 60 mg/kg, at least about 75 mg/kg, at least about 100 mg/kg, at least about 125 mg/kg, at least about 150 mg/kg, at least about 175 mg/kg, at least about 200 mg/kg, at least about 300 mg/kg, or at least about 400 mg/kg. In certain embodiments, the administered dose is no more than about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 75 mg/kg, about 100 mg/kg, about 125 mg/kg, about 150 mg/kg, about 175 mg/kg, about 200 mg/kg, about 300 mg/kg, about 400 mg/kg, about 500 mg/kg, about 600 mg/kg, about 700 mg/kg, about 800 mg/kg, about 900 mg/kg, about 1000 mg/kg, about 1100 mg/kg, about 1200 mg/kg, or about 1300 mg/kg. It is understood that any of the lower limit values and upper limit values can be combined to create a range. In certain embodiments, the administered dose is at least 75 mg/kg or 100 mg/kg or the rat equivalent to about, at least, 12.2 or 16.2 mg/kg/day in humans, or at least 85 mg/kg over a week period, or at least 113 mg/kg over a week period.

In one embodiment, the formulation, preferably, the CoQ10 formulation, is administered one time per week. In one embodiment, the formulation, preferably, the CoQ10 formulation, is administered 3 times per week. In another embodiment, the formulation, preferably, the CoQ10 formulation, is administered 5 times per week. In one embodiment, the formulation, preferably, the CoQ10 formulation, is administered once per day. In some embodiments, where the formulation is an IV formulation administered by infusion, the dosage is administered by infusion over about 1 hour, 2 hours, 3 hours, 4 hours or longer. In one embodiment, the IV formulation is administered by infusion over about 4 hours.

In certain embodiments, the formulation, preferably, a CoQ10 formulation, can be administered in one or more cycles. For example, the CoQ10 can be administered for 2, 3, 4, 5, 6, 7, 8, or more weeks consecutively, and then not administered for a period of 1, 2, 3, 4, or more weeks, providing a cycle of administration. The number of cycles of administration depends, for example, on the response of the subject, the severity of disease, and other therapeutic interventions used on the subject.

In another embodiment, the formulation, preferably, a CoQ10 formulation, is administered in the form of a CoQ10 IV formulation at a dosage of between about 10 mg/kg and about 10,000 mg/kg of CoQ10, about 20 mg/kg to about 5000 mg/kg, about 50 mg/kg to about 3000 mg/kg, about 100 mg/kg to about 2000 mg/kg, about 200 mg/kg to about 1000 mg/kg, about 300 mg/kg to about 500 mg/kg, or about 55 mg/kg to about 110 mg/kg wherein the CoQ10 formulation comprises between about 1% and 10% of CoQ10. In one embodiment, the CoQ10 formulation comprises about 4% of CoQ10. In one embodiment, the CoQ10 IV formulation comprises about 8% of CoQ10. In other embodiments, the CoQ10 IV formulation comprises about 0.1%, 0.2%. 0.3%, 0.4%. 0.5%, 0.6%, 0.7%, 0.8%. 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% of CoQ10. It should be understood that ranges having any one of these values as the upper or lower limits are also intended to be part of this invention.

In the treatment of CNS cancers, the formulations may be in a pharmaceutically acceptable carrier that may be administered in a therapeutically effective amount to a subject as either a mono-therapy, in combination with at least one other chemotherapeutic agent for a given indication, in combination with radiotherapy, following surgical intervention to radically remove a tumor, in combination with other alternative and/or complementary acceptable treatments for cancer, and the like.

In general, the CoQ10 formulation described herein may be used to prophylactically or therapeutically treat any neoplasm. In a particular embodiment, the formulation is used to treat CNS tumors including both primary and secondary CNS tumors. It is understood that those suffering from a secondary CNS neoplasm are likely suffering from neoplasia at one or more other sites in the body. In one embodiment, the CoQ10 formulations described herein may be used to treat a chloroleukemia, e.g., a secondary or metastatic chloroleukemia, e.g., that presents, migrates or metastasizes to the central nervous system.

In certain embodiments, the effect CoQ10 may have on cancer cells may depend, in part, on the various states of metabolic and oxidative flux exhibited by the cancer cells. CoQ10 may be utilized to interrupt and/or interfere with the conversion of an oncogenic cell's dependency of glycolysis and increased lactate utility. As it relates to a cancer state, this interference with the glycolytic and oxidative flux of the tumor microenvironment may influence apoptosis and angiogenesis in a manner which reduces the development of a cancer cell. In some embodiments, the interaction of CoQ10 with glycolytic and oxidative flux factors may enhance the ability of CoQ10 to exert its restorative apoptotic effect in cancer. While the present disclosure has focused on CoQ10 and its metabolites, other compounds related to CoQ10 which may be administered instead of, or in combination with, CoQ10 include, but are not limited to, benzoquinones, isoprenoids, farnesols, farnesyl acetate, farnesyl pyrophosphate, 1-phenylalanine, d-phenylalanine, dl-phenylalanine, l-tyrosine, d-tyrosine, dl-tyrosine, 4-hydroxy-phenylpyruvate, 4-hydroxy-phenyllactate, 4-hydroxy-cinnamate, dipeptides and tripeptides of tyrosine or phenylalanine, 3,4-dihydroxymandelate, 3-methoxy-4-hydroxyphenylglycol, 3-methoxy-4-hydroxymandelate, vanillic acid, phenylacetate, pyridoxine, S-adenosyl methionine, panthenol, mevalonic acid, isopentyl pyrophosphate, phenylbutyrate, 4-hydroxy-benzoate, decaprenyl pyrophosphate, beta-hydroxybutyrate, 3-hydroxy-3-methyl-glutarate, acetylcarnitine, acetoacetylcarnitine, acetylglycine, acetoacetylglycine, carnitine, acetic acid, pyruvic acid, 3-hydroxy-3-methylglutarylcarnitine, all isomeric forms of serine, alanine, cysteine, glycine, threonine, hydroxyproline, lysine, isoleucine, and leucine, even carbon number C4 to C8 fatty acids (butyric, caproic, caprylic, capric, lauric, myristic, palmitic, and stearic acids) salts of carnitine and glycine, e.g., palmitoylcarnitine and palmitoylglycine, and 4-hydroxy-benzoate polyprenyltransferase, any salts of these compounds, as well as any combinations thereof, and the like.

In one embodiment, administration of CoQ10 as described herein, reduces CNS tumor size, inhibits CNS tumor growth and/or prolongs the survival time of a CNS tumor-bearing subject as compared to an appropriate control. Accordingly, this invention also relates to a method of treating CNS tumors in a human or other animal by administering to such human or animal an effective, non-toxic amount of CoQ10. For example, by administering an effective dose by IV administration. Or, for example, by administering an effective dose by topical administration. One skilled in the art would be able, by routine experimentation with the guidance provided herein, to determine what an effective, non-toxic amount of CoQ10 would be for the purpose of treating malignancies. For example, a therapeutically active amount of CoQ10 may vary according to factors such as the disease stage (e.g., stage I versus stage IV), age, sex, medical complications (e.g., immunosuppressed conditions or diseases) and weight of the subject, and the ability of the CoQ10 to elicit a desired response in the subject. The dosage regimen may be adjusted to provide the optimum therapeutic response. For example, several divided doses may be administered daily, or the dose may be proportionally reduced as indicated by the exigencies of the therapeutic situation.

In certain embodiments of the invention, the methods further include a treatment regimen which includes any one of or a combination of surgery, radiation, hormone therapy, antibody therapy, therapy with growth factors, cytokines, and chemotherapy.

It is understood that such treatment methods can similarly be performed by administration of CoQ10 precursors, metabolites, and related compounds.

VI. Prevention and Treatment of Secondary Malignancies

While prognosis of childhood cancers, particularly childhood leukemias is quite high, long-term survivors are increasingly experiencing late effects of treatment. For example, a study of 9720 children given a diagnosis of acute lymphoblastic leukemia in 1972-1988 treated with the standard of care were found to have a 7 fold excess of all cancers and a 22-fold excess of neoplasms of the CNS at a median follow-up of 4.7 years (Neglia et al., NEJM, 325:1330-1336, 1991, incorporated herein by reference). The British Childhood Cancer Survivor Study, a national, population-based, cohort study of 17,980 individuals surviving at least 5 years after diagnosis of childhood cancer identified 247 secondary primary neoplasms (SPNs) of the CNS. In the study, the risk of meningioma was found to increase rapidly with increased dose of radiation to meningeal tissue, up to a 479-fold increase, and with increased dose of intrathecal methotrexate, up to a 36-fold increase, as compared to the general population (Taylor et al., *J Clin Oncol* 28:5287-5293, 2010, incorporated herein by reference). Longer periods of follow-up revealed even greater incidences of secondary tumors, particularly secondary CNS tumors. For example, a study of 1612 consecutively enrolled patients treated for acute lymphocytic leukemia (ALL) had a cumulative incidence of brain tumors at 20 years of 1.39% (Walter et al., *J Clin Oncol.*, 16:3761-3767, 1998, incorporated herein by reference). Hijiya et al., 2007, (JAMA, 297:1207-1215, incorporated herein by reference) reported on a retrospective study of 2169 patients with acute lymphoblastic leukemia treated between 1962 and 1998 who achieved complete remission and had a median follow-up time of 18.7 years (range, 2.4-41.3 years). Secondary neoplasms developed as the first event in 123 patients and comprised 46 myeloid malignancies, 3 lymphomas, 14 basal cell carcinomas, 16 other carcinomas, 6 sarcomas, 16 meningiomas, and 22 other brain tumors providing a cumulative incidence of secondary neoplasm was 4.17% (SE, 0.46%) at 15 years and increased substantially after 20 years, reaching 10.85% (SE, 1.27%) at 30 years. The cumulative incidence of each tumor type at 30 years was 2.19% (SE, 0.32%) for myeloid malignancy, 0.17% (SE, 0.10%) for lymphoma, 3.00% (SE, 0.59%) for brain tumor, 4.91% (SE, 1.04%) for carcinoma, and 0.57% (SE, 0.37%) for sarcoma. The cumulative incidence of secondary neoplasms was demonstrated to increase steadily over 30 years after treatment of ALL.

Secondary tumors are also observed in subjects treated for adult tumors. However, due to the long latency period, such tumors are less frequently observed.

In certain embodiments, the CoQ10 compounds provided herein can be used to prevent and/or treat secondary tumors after treatment and remission of the primary tumors. In certain embodiments, the methods can be used for the prevention of all types of secondary tumors. In certain embodiments, the methods can be used for the prevention of secondary CNS tumors. In certain embodiments, the methods can be used for the treatment of secondary tumors. The secondary tumors include, for example, secondary tumors of the CNS. The secondary tumors of the CNS can be identified, for example, by monitoring a subject who is at high risk for development of a secondary CNS tumor, e.g., a subject who is in remission from a pediatric tumor, particularly a pediatric leukemia, particularly when the subject was treated with radiation to the CNS or with chemotherapeutic agents delivered to the CNS, for the development of a CNS abnormality. The CNS abnormality can be detected by functional testing, reporting or identification of CNS abnormalities, e.g., headache, seizure, or imaging analysis.

The Examples demonstrate that the CoQ10 compounds provided herein are useful for the treatment of such secondary tumors. Specifically, in the examples, leukemia was induced in rats that were subsequently treated for the leukemia. As a result of the treatment, about half of the rats survived and entered remission. However, over time, about 20% of the surviving rats developed CNS tumors as demonstrated by the appearance of CNS abnormalities. That is, the rats developed secondary CNS tumors which were effectively treated with the CoQ10 compounds provided herein.

As the CoQ10 compounds provided herein do not demonstrate significant toxicities, the compounds could be used to prevent the development of secondary tumors, including secondary CNS tumors, by administration of a CoQ10 compound to a subject at the conclusion of treatment for the primary tumor, e.g., the primary leukemia. Administration of the CoQ10 compound can be initiated at any time after the conclusion of the treatment of the leukemia, e.g., at a specific time interval, e.g., one month, six months, one year, two years, three years, five years, ten years, etc.; or after a specific event, e.g., after confirmation of remission, or a certain time interval after confirmation of remission, e.g., one month, six months, one year, two years, three years, five years, ten years, etc. after remission. The CoQ10 compounds can be administered using the methods and formulations provided herein.

VII. Combination Therapies

In certain embodiments, the formulations of the invention, e.g., the CoQ10 formulations, can be used in combination therapy with at least one other therapeutic agent. In preferred embodiments, CoQ10 is administered in an amount that would be therapeutically effective if delivered alone, i.e., CoQ10 is a therapeutic agent, not predominantly an agent to ameliorate side effects of other chemotherapy or other cancer treatments. CoQ10 and/or pharmaceutical formulations thereof and the other therapeutic agent can act additively or, more preferably, synergistically. In one embodiment, CoQ10 and/or a formulation thereof is administered concurrently with the administration of another therapeutic agent. In another embodiment, a compound and/or pharmaceutical formulation thereof is administered prior or subsequent to administration of another therapeutic agent. In one embodiment, the CoQ10 and additional therapeutic agent active synergistically. In one embodiment, the CoQ10 and additional therapeutic agent act additively.

In one embodiment, the therapeutic methods of the invention further comprise administration of one or more additional agents, e.g., one or more therapeutic agents. For example, in one embodiment, an additional agent for use in the therapeutic methods of the invention is a chemotherapeutic agent.

Chemotherapeutic agents generally belong to various classes including, for example: 1. Topoisomerase II inhibitors (cytotoxic antibiotics), such as the anthracyclines/anthracenediones, e.g., doxorubicin, epirubicin, idarubicin and nemorubicin, the anthraquinones, e.g., mitoxantrone and losoxantrone, and the podophillotoxines, e.g., etoposide and teniposide; 2. Agents that affect microtubule formation (mitotic inhibitors), such as plant alkaloids (e.g., a compound belonging to a family of alkaline, nitrogen-containing molecules derived from plants that are biologically active and cytotoxic), e.g., taxanes, e.g., paclitaxel and docetaxel, and the vinka alkaloids, e.g., vinblastine, vincristine, and vinorelbine, and derivatives of podophyllotoxin; 3. Alkylating agents, such as nitrogen mustards, ethyleneimine compounds, alkyl sulphonates and other compounds with an alkylating action such as nitrosoureas, dacarbazine, cyclophosphamide, ifosfamide and melphalan; 4. Antimetabolites (nucleoside inhibitors), for example, folates, e.g., folic acid, fiuropyrimidines, purine or pyrimidine analogues such as 5-fluorouracil, capecitabine, gemcitabine, methotrexate, and edatrexate; 5. Topoisomerase I inhibitors, such as topotecan, irinotecan, and 9-nitrocamptothecin, camptothecin derivatives, and retinoic acid; and 6. Platinum compounds/complexes, such as cisplatin, oxaliplatin, and carboplatin; Exemplary chemotherapeutic agents for use in the methods of the invention include, but are not limited to, amifostine (ethyol), cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), doxorubicin lipo (doxil), gemcitabine (gemzar), daunorubicin, daunorubicin lipo (daunoxome), procarbazine, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-I1, 1O-hydroxy-7-ethyl-camptothecin (SN38), dacarbazine, S-I capecitabine, ftorafur, 5'deoxyflurouridine, UFT, eniluracil, deoxycytidine, 5-azacytosine, 5-azadeoxycytosine, allopurinol, 2-chloro adenosine, trimetrexate, aminopterin, methylene-10-deazaaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10, 11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab, 5-Fluorouracil, Capecitabine, Pentostatin, Trimetrexate, Cladribine, floxuridine, fludarabine, hydroxyurea, ifosfamide, idarubicin, mesna, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, cisplatin, doxorubicin, paclitaxel (taxol), bleomycin, mTor, epidermal growth factor receptor (EGFR), and fibroblast growth factors (FGF) and combinations thereof which are readily apparent to one of skill in the art based on the appropriate standard of care for a particular tumor or cancer.

In another embodiment, an additional agent for use in the combination therapies of the invention is a biologic agent.

Biologic agents (also called biologics) are the products of a biological system, e.g., an organism, cell, or recombinant system. Examples of such biologic agents include nucleic acid molecules (e.g., antisense nucleic acid molecules), interferons, interleukins, colony-stimulating factors, antibodies, e.g., monoclonal antibodies, anti-angiogenesis agents, and cytokines. Exemplary biologic agents are discussed in more detail below and generally belong to various classes including, for example: 1. Hormones, hormonal analogues, and hormonal complexes, e.g., estrogens and estrogen analogs, progesterone, progesterone analogs and progestins, androgens, adrenocorticosteroids, antiestrogens, antiandrogens, antitestosterones, adrenal steroid inhibitors, and anti-leutinizing hormones; and 2. Enzymes, proteins, peptides, polyclonal and/or monoclonal antibodies, such as interleukins, interferons, colony stimulating factor, etc.

In one embodiment, the biologic is an interferon. Interferons (IFN) are a type biologic agent that naturally occurs in the body. Interferons are also produced in the laboratory and given to cancer patients in biological therapy. They have been shown to improve the way a cancer patient's immune system acts against cancer cells.

Interferons may work directly on cancer cells to slow their growth, or they may cause cancer cells to change into cells with more normal behavior. Some interferons may also stimulate natural killer cells (NK) cells, T cells, and macrophages which are types of white blood cells in the bloodstream that help to fight cancer cells.

In one embodiment, the biologic is an interleukin. Interleukins (IL) stimulate the growth and activity of many immune cells. They are proteins (cytokines and chemokines) that occur naturally in the body, but can also be made in the laboratory.

Some interleukins stimulate the growth and activity of immune cells, such as lymphocytes, which work to destroy cancer cells.

In another embodiment, the biologic is a colony-stimulating factor.

Colony-stimulating factors (CSFs) are proteins given to patients to encourage stem cells within the bone marrow to produce more blood cells. The body constantly needs new white blood cells, red blood cells, and platelets, especially when cancer is present. CSFs are given, along with chemotherapy, to help boost the immune system. When cancer patients receive chemotherapy, the bone marrow's ability to produce new blood cells is suppressed, making patients more prone to developing infections. Parts of the immune system cannot function without blood cells, thus colony-stimulating factors encourage the bone marrow stem cells to produce white blood cells, platelets, and red blood cells.

With proper cell production, other cancer treatments can continue enabling patients to safely receive higher doses of chemotherapy.

In another embodiment, the biologic is an antibody. Antibodies, e.g., monoclonal antibodies, are agents, produced in the laboratory, that bind to cancer cells.

Monoclonal antibody agents do not destroy healthy cells. Monoclonal antibodies achieve their therapeutic effect through various mechanisms. They can have direct effects in producing apoptosis or programmed cell death. They can block growth factor receptors, effectively arresting proliferation of tumor cells. In cells that express monoclonal antibodies, they can bring about anti-idiotype antibody formation.

Examples of antibodies which may be used in the combination treatment of the invention include anti-CD20 antibodies, such as, but not limited to, cetuximab, Tositumomab, rituximab, and Ibritumomab. Anti-HER2 antibodies may also be used in combination with an environmental influencer for the treatment of cancer. In one embodiment, the anti-HER2 antibody is Trastuzumab (Herceptin). Other examples of antibodies which may be used in combination with an environmental influencer for the treatment of cancer include anti-CD52 antibodies (e.g., Alemtuzumab), anti-CD-22 antibodies (e.g., Epratuzumab), and anti-CD33 antibodies (e.g., Gemtuzumab ozogamicin). Anti-VEGF antibodies may also be used in combination with an environmental influencer for the treatment of cancer. In one embodiment, the anti-VEGF antibody is bevacizumab. In other embodiments, the biologic agent is an antibody which is an anti-EGFR antibody e.g., cetuximab. Another example is the anti-glycoprotein 17-1A antibody edrecolomab. Numerous other anti-tumor antibodies are known in the art and would be understood by the skilled artisan to be encompassed by the present invention.

In another embodiment, the biologic is a cytokine. Cytokine therapy uses proteins (cytokines) to help a subject's immune system recognize and destroy those cells that are cancerous. Cytokines are produced naturally in the body by the immune system, but can also be produced in the laboratory. This therapy is used with advanced melanoma and with adjuvant therapy (therapy given after or in addition to the primary cancer treatment). Cytokine therapy reaches all parts of the body to kill cancer cells and prevent tumors from growing.

In another embodiment, the biologic is a fusion protein. For example, recombinant human Apo2L/TRAIL (GENETECH) may be used in a combination therapy. Apo2/TRAIL is the first dual pro-apoptotic receptor agonist designed to activate both pro-apoptotic receptors DR4 and DR5, which are involved in the regulation of apoptosis (programmed cell death).

In one embodiment, the biologic is an antisense nucleic acid molecule.

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

In one embodiment, a biologic agent is an siRNA molecule, e.g., of a molecule that enhances angiogenesis, e.g., bFGF, VEGF and EGFR. In one embodiment, a biologic agent that inhibits angiogenesis mediates RNAi. RNA interference (RNAi) is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. Cell 101, 25-33 (2000). Tuschl, T. et al. Genes Dev. 13, 3191-3197 (1999); Cottrell T R, and Doering T L. 2003. Trends Microbiol. 11:37-43; Bushman F. 2003. MoI Therapy. 7:9-10; McManus M T and Sharp P A. 2002. Nat Rev Genet. 3.737-47). The process occurs when an endogenous ribonuclease cleaves the longer dsRNA into shorter, e.g., 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs® or Ambion®. In one embodiment one or more chemistries for use in antisense RNA can be employed in molecules that mediate RNAi.

In another embodiment, an antisense nucleic acid of the invention is a compound that mediates RNAi. RNA interfering agents include, but are not limited to, nucleic acid molecules including RNA molecules which are homologous to the target gene or genomic sequence, "short interfering RNA" (siRNA), "short hairpin" or "small hairpin RNA" (shRNA), and small molecules which interfere with or inhibit expression of a target gene by RNA interference (RNAi). RNA interference is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. Cell 101, 25-33 (2000). Tuschl, T. et al. Genes Dev. 13, 3191-3197 (1999)). The process occurs when an endogenous ribonuclease cleaves the longer dsRNA into shorter, 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs and Ambion. In one embodiment one or more of the chemistries described above for use in antisense RNA can be employed.

Exemplary biologic agents for use in the methods of the invention include, but are not limited to, gefitinib (Iressa), anastrazole, diethylstilboesterol, estradiol, premarin, raloxifene, progesterone, norethynodrel, ethisterone, dimethisterone, megestrol acetate, medroxyprogesterone acetate, hydroxyprogesterone caproate, norethisterone, methyltestosterone, testosterone, dexamethasone, prednisone, Cortisol, solumedrol, tamoxifen, fulvestrant, toremifene, aminoglutethimide, testolactone, droloxifene, anastrozole, bicalutamide, flutamide, nilutamide, goserelin, flutamide, leuprolide, triptorelin, aminoglutethimide, mitotane, goserelin, cetuximab, erlotinib, imatinib, Tositumomab, Alemtuzumab, Trastuzumab, Gemtuzumab, Rituximab, Ibritumomab tiuxetan, Bevacizumab, Denileukin diftitox, Daclizumab, interferon alpha, interferon beta, anti-4-1BB, anti-4-1BBL, anti-CD40, anti-CD 154, anti-OX40, anti-OX40L, anti-CD28, anti-CD80, anti-CD86, anti-CD70, anti-CD27, anti-HVEM, anti-LIGHT, anti-GITR, anti-GITRL, anti-CTLA-4, soluble OX40L, soluble 4-IBBL, soluble CD154, soluble GITRL, soluble LIGHT, soluble CD70, soluble CD80, soluble CD86, soluble CTLA4-Ig, GVAX®, and combinations thereof which are readily apparent to one of skill in the art based on the appropriate standard of care for a particular tumor or cancer. The soluble forms of agents may be made as, for example fusion proteins, by operatively linking the agent with, for example, Ig-Fc region.

It should be noted that more than one additional agent, e.g., 1, 2, 3, 4, 5, may be administered in combination with the CoQ10 formulations provided herein. For example, in one embodiment two chemotherapeutic agents may be administered in combination with CoQ10. In another embodiment, a chemotherapeutic agent, a biologic agent, and CoQ10 may be administered. Appropriate doses and routes of administration of the chemotherapeutic agents provided herein are known in the art.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

EXAMPLES

Example 1—Treatment of Central Nervous System Chloroleukemias Using Coenzyme Q10

A model of CNS chloroleukemia was created using Fischer 344 rats, in which chloroleukemic cells were injected into the rats as newborns and lipopolysaccharide (LPS) was given as a first-line of treatment. The cure rate with this regimen was approximately 50%, and approximately 10% of survivors developed CNS leukemia as judged by their motor skills and the presence of quadriplegia and paraplegia.

For this study, 2400 Fischer 344 neonates were injected with the chloroleukemic cell line MIAC51 and treated with LPS. All animals with overt signs of leukemia, i.e., systemic disease, were sacrificed by day 26. By day 35, survivors started exhibiting CNS abnormalities suggesting that the tumor was localized to the CNS. Of that cohort, 150 animals were selected with hind leg paraplegia on day 40, see FIGS. 1A and 1B. These animals were then re-randomized into 5 groups: group 1 received no treatment, group 2 received excipient control IV, group 3 received 5 mg/kg CoQ10 IV (i.e., 15 mg/kg/day), group 4 received 10 mg/kg IV (i.e., 30 mg/kg/day), and group 5 received 25 mg/kg IV (i.e., 75 mg/kg/day) for 4 weeks, 3 times daily.

Figure 2:
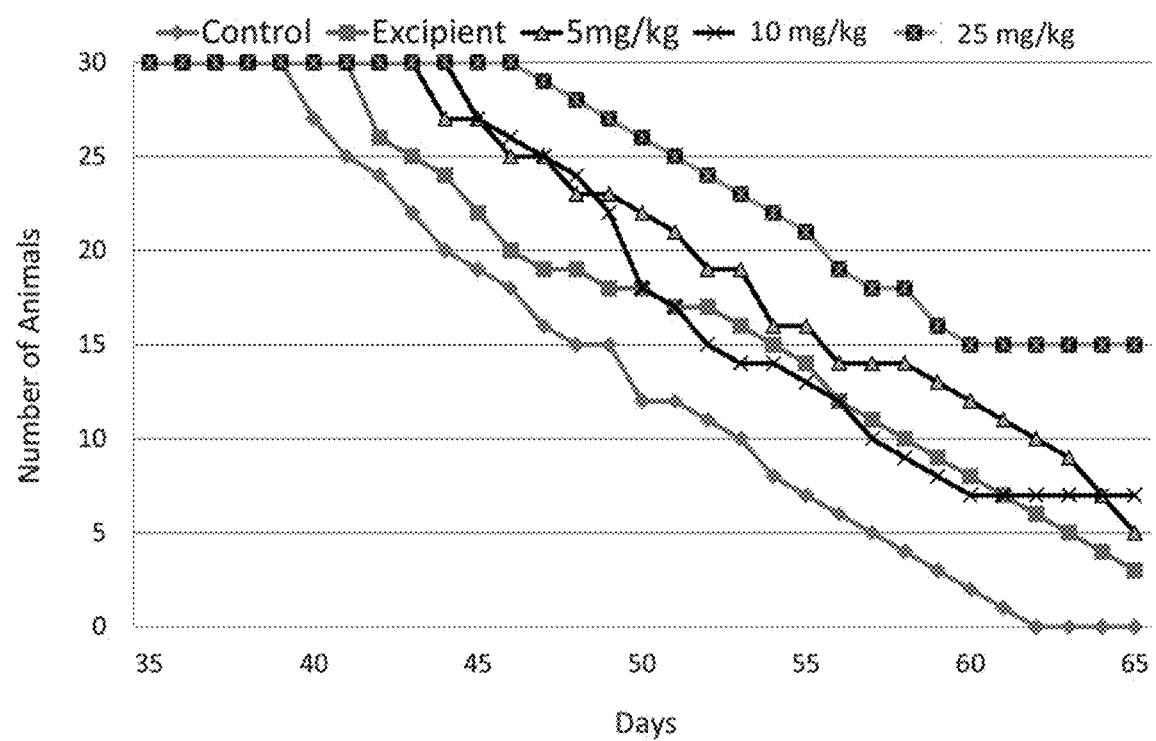
FIG. 2: Mortality Curves for animals treated with or without CoQ10. A decrease in mortality due to CNS tumors is observed in a dose-dependent manner with CoQ10.
Figure 3A:
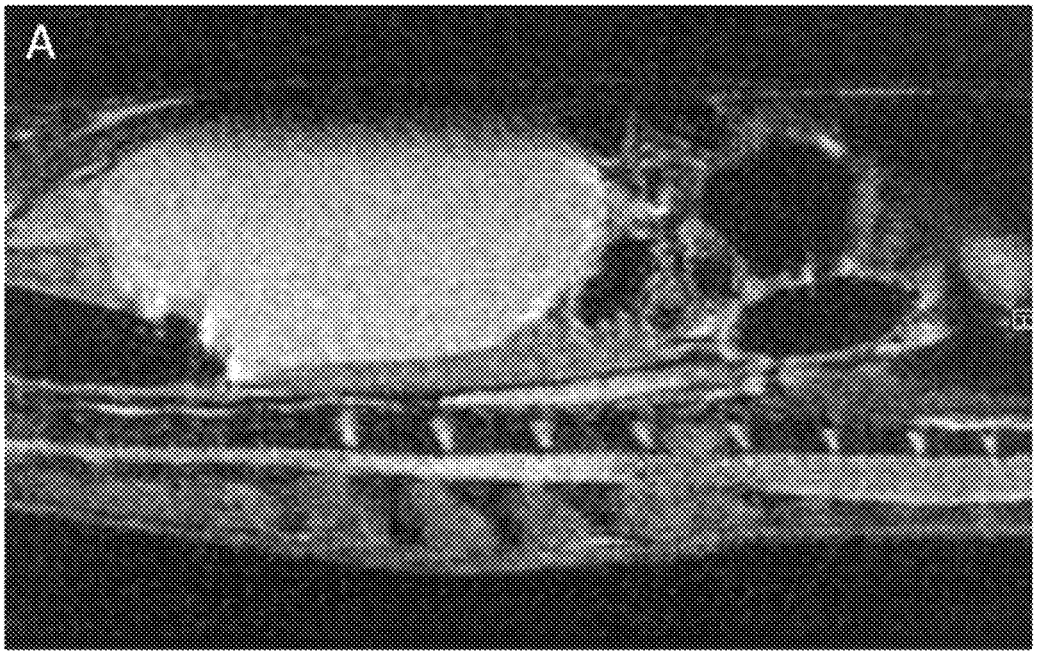
FIGS. 3A and 3B: MRI imaging of lesions depicting the chloroma in the spinal area before (A) and after CoQ10 treatment (B) in the same animal.
Figure 3B:
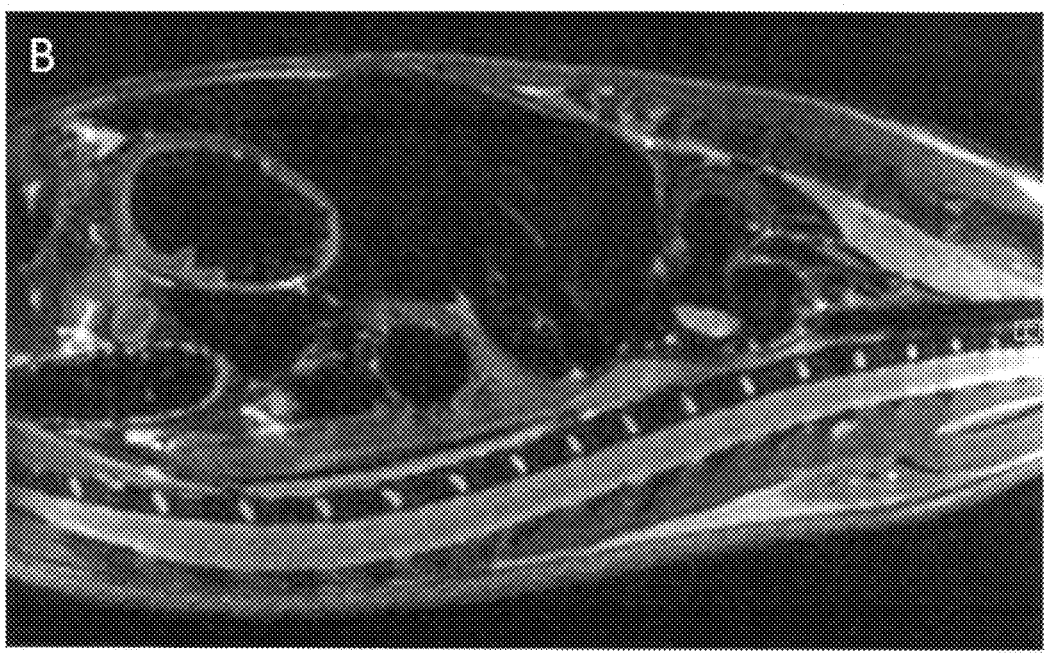

Rats in groups 1, 2, 3 and 4 did not exhibit any signs of improvement and were sacrificed due to metastatic malignancy and severe CNS abnormalities, e.g., resulting in decreased muscle control, lack of coordination, weakness, paralysis, difficulties in walking that prevented the rats from eating or performing self care (FIG. 2). These findings were recorded by MRI positive for tumor cells. In sharp contrast, animals injected with 25 mg/kg IV three times per day (i.e., 75 mg/kg/day) exhibited a significant recovery of their motor skills and regained their ability to walk. MRI distinctly shows the lack of tumor cells in this group (FIGS. 3A and B). Taken together, these results strongly indicate that CoQ10 is an effective treatment for CNS leukemia and may also be an effective prophylactic agent to prevent the extravasation of leukemic cells in the CNS, thereby preventing, delaying, or limiting the formation of secondary tumors.

Example 2—Long Term Effect of CoQ10 Treatment of Central Nervous System Chloroleukemias The model of CNS chloroleukemia in Fischer 344 rats provided in Example 1 was used for long term studies of the treatment of metastatic, leukemic CNS tumors. As in Example 1 chloroleukemic cells were injected into the rats as newborns and lipopolysaccharide (LPS) was given as a first-line of treatment. The cure rate with this regimen was approximately 50%, and approximately 10% of survivors developed CNS leukemia as judged by their motor skills and the presence of quadriplegia and paraplegia.

For this study of long term effect of CoQ10 on CNS leukemia, 300 paraplegic animals with overt CNS leukemia were randomized into two groups of 150 animals each. Group one received a saline control. Group two received 100 mg/kg CoQ10 once daily starting on day 1 through day 28 (first cycle). The second cycle started on day 35 and continued through day 62. In this study, animals received two cycles of 28 days of CoQ10.

Figure 4:
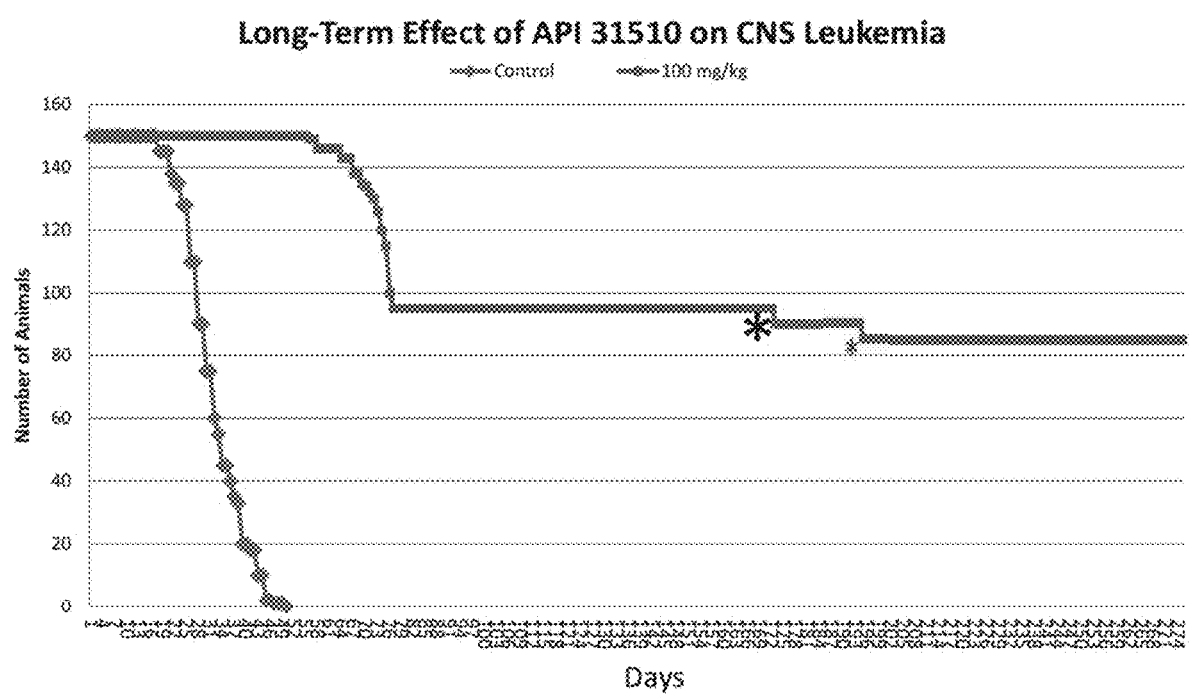
FIG. 4: Long-term Effect of CoQ10 on CNS Leukemia. 300 paraplegic animals with overt CNS leukemia were randomized into two groups of 150 animals each: one received phosphate buffered saline (PBS) and the other group received 100 mg/kg CoQ10 once daily starting on day 1 through day 28 (first cycle). A second cycle of 100 mg/kg CoQ10 once daily started on day 35 and continued through day 62. Animals received two cycles of 28 days each of CoQ10. On days 173 and 195 as indicated by *, 5 animals were sacrificed for necropsy and pathology analysis.

Rats in the control groups did not exhibit any signs of improvement and were sacrificed due to metastatic malignancy and severe CNS abnormalities, e.g., resulting in decreased muscle control, lack of coordination, weakness, paralysis, difficulties in walking that prevented the rats from eating or performing self care (FIG. 4). In sharp contrast, animals injected with 100 mg/kg IV exhibited a significant recovery of their motor skills and regained their ability to walk. On days 173 and 195 five (5) animals which were treated with 100 mg/kg CoQ10 were sacrificed for necropsy and pathological analysis. No evidence of chloroleukemia or CNS tumors were found Taken together, these results strongly indicate that CoQ10 is an effective treatment for CNS leukemia and may also be an effective prophylactic agent to prevent the extravasation of leukemic cells in the CNS, thereby preventing, delaying, or limiting the formation of secondary tumors.

The invention claimed is:

1. A method of treating a central nervous system (CNS) tumor in a subject exhibiting at least one CNS abnormality as a result of the presence of the CNS tumor comprising administering to the subject a composition comprising a Coenzyme Q10 (CoQ10) compound, thereby treating the CNS tumor, wherein the at least one CNS abnormality exhibited by the subject as a result of the presence of the CNS tumor comprises decreased muscle control, and treatment of the subject results in amelioration of the decreased muscle control in the subject.

2. The method of claim 1, wherein the at least one CNS abnormality further comprises a CNS abnormality selected from the group consisting of a headache, a seizure, a change in memory, loss of short term memory, a change in temperament, sudden onset of panic attacks induced by familiar situations, a change in intellectual function, inability to do math, inability to find objects in plain sight; confusion, disorientation, becoming lost in a familiar location; blurred vision, loss of vision, loss of peripheral vision, double vision, dizziness, hearing problems, ringing in ears, buzzing in ears, lack of coordination, decreased sensation, weakness, paralysis, paraplegia, quadriplegia, difficulty with walking, change in gait, difficulty with speech, and balance problems.

3. The method of claim 1, wherein the at least one CNS abnormality comprises at least 2 CNS abnormalities.

4. The method of claim 1, wherein the at least one CNS abnormality comprises 3-10 CNS abnormalities.

5. A method of treatment of a secondary CNS tumor from a primary tumor in a subject exhibiting at least one CNS abnormality as a result of the presence of the secondary CNS tumor comprising administering to the subject a composition comprising a Coenzyme Q10 (CoQ10) compound, thereby treating the secondary CNS tumor, wherein the at least one CNS abnormality exhibited by the subject as a result of the presence of the secondary CNS tumor comprises decreased muscle control, and treatment of the subject results in amelioration of the decreased muscle control in the subject.

6. The method of claim 5, wherein the primary tumor is a pediatric tumor.

7. The method of claim 6, wherein the pediatric tumor is a leukemia.

8. The method of claim 5, wherein the primary tumor was treated with CNS radiation.

9. The method of claim 5, wherein the primary tumor was treated by administration of a chemotherapeutic agent to the CNS.

10. The method of claim 5, wherein the secondary tumor is identified at least one year after treatment of the primary tumor is concluded.

11. The method of claim 5, wherein the secondary tumor is identified at least three years after treatment of the primary tumor is concluded.

12. The method of claim 5, wherein the secondary tumor is identified at least five years after treatment of the primary tumor is concluded.

13. The method of claim 5, wherein the secondary tumor is identified at least ten years after treatment of the primary tumor is concluded.

14. The method of claim 1, wherein the CoQ10 compound is CoQ10.

15. The method of claim 1, wherein the tumor is a leukemic tumor.

16. The method of claim 1, wherein the CoQ10 compound is administered topically.

17. The method of claim 1, wherein the CoQ10 compound is administered parenterally.

18. The method of claim 1, wherein the CoQ10 compound is administered by injection or infusion.

19. The method of claim 18, wherein the CoQ10 compound is not administered directly to the CNS.

20. The method of claim 1, further comprising administration of an additional agent.

21. The method of claim 20, wherein the additional agent is a chemotherapeutic agent for treatment of a tumor.

22. The method of claim 1, wherein the tumor is further treated with radiation therapy.

23. The method of claim 1, wherein the tumor is further treated with surgery.

24. The method of claim 1, wherein the subject is human.

25. The method of claim 5, wherein the CoQ10 compound is CoQ10.

26. The method of claim 5, wherein the CoQ10 compound is administered by injection or infusion.

27. The method of claim 5, wherein the subject is human.

* * * * *